US011728035B1

(12) United States Patent
Douglas et al.

(10) Patent No.: US 11,728,035 B1
(45) Date of Patent: Aug. 15, 2023

(54) RADIOLOGIST ASSISTED MACHINE LEARNING

(71) Applicants: Robert Edwin Douglas, Winter Park, FL (US); David Byron Douglas, Winter Park, FL (US); Kathleen Mary Douglas, Winter Park, FL (US)

(72) Inventors: Robert Edwin Douglas, Winter Park, FL (US); David Byron Douglas, Winter Park, FL (US); Kathleen Mary Douglas, Winter Park, FL (US)

(*) Notice: Subject to any disclaimer, the term of this patent is extended or adjusted under 35 U.S.C. 154(b) by 0 days.

(21) Appl. No.: 17/888,432

(22) Filed: Aug. 15, 2022

Related U.S. Application Data

(63) Continuation of application No. 16/939,192, filed as application No. PCT/US2019/023968 on Mar. 26, 2019, now abandoned, which is a continuation-in-part of application No. 16/843,988, filed on Apr. 9, 2020, now Pat. No. 10,964,124, and a continuation-in-part of application No. 16/752,662, filed on Jan. 26, 2020, now Pat. No. 10,657,731, and a continuation-in-part of application No. 16/195,251, filed on Nov. 19, 2018, now Pat. No. 10,878,639, and a continuation-in-part of application No. 15/904,092, filed on Feb. 23, 2018, now Pat. No. 10,586,400.

(60) Provisional application No. 62/748,555, filed on Oct. 22, 2018, provisional application No. 62/695,868, filed on Jul. 10, 2018, provisional application No. 62/651,934, filed on Apr. 3, 2018, provisional application No. 62/628,527, filed on Feb. 9, 2018.

(51) Int. Cl.
G16H 50/20 (2018.01)
G16H 30/20 (2018.01)

(52) U.S. Cl.
CPC ............ G16H 50/20 (2018.01); G16H 30/20 (2018.01)

(58) Field of Classification Search
None
See application file for complete search history.

(56) References Cited

U.S. PATENT DOCUMENTS

| 9,589,374 B1* | 3/2017 | Gao ..................... A61B 6/5211 |
| 2016/0026266 A1* | 1/2016 | Douglas ................. A61B 6/466 |
| | | 345/157 |
| 2016/0171682 A1* | 6/2016 | Abedini ................. G16H 30/20 |
| | | 382/132 |
| 2018/0005417 A1* | 1/2018 | Schieke ................ G06T 11/008 |
| 2018/0008220 A1* | 1/2018 | Boone .................. A61B 8/4416 |
| 2018/0315188 A1* | 11/2018 | Tegzes ..................... G06T 7/11 |
| 2019/0122073 A1* | 4/2019 | Ozdemir ................ G06V 20/56 |
| 2019/0209116 A1* | 7/2019 | Sjöstrand ................. G16H 50/30 |
| 2020/0286614 A1* | 9/2020 | Do ......................... G16H 30/40 |

* cited by examiner

Primary Examiner — James A Thompson

(57) ABSTRACT

A computerized medical diagnostic system uses a training dataset that is updated based on reports generated by a radiologist. AI and/or CAD is used to make an initial determination of no finding, finding, or diagnosis based on the training dataset. Normal results with a high confidence of no finding are not reviewed by the radiologist. Low confidence results, findings, and diagnosis are reviewed by the radiologist. The radiologist generates a report that associates terminology and weighting with marked 3D image volumes. The report is used to update the training dataset.

20 Claims, 20 Drawing Sheets

ILLUSTRATION OF THE KEY COMPONENTS FOR AN INTEGRATED
RADIOLOGIST-ASSISTED MACHINE LEARNING PROCESS

ILLUSTRATION OF PRESENTATION OF PERTINENT PATIENT DATA
IDENTIFIED VIA AI SEARCH THROUGH THE ELECTRONIC MEDICAL RECORD
THAT MAY BE RELEVANT TO THE AREA OF INTEREST BEING EXAMINED

ILLUSTRATION OF 3D CURSOR USE IN CONJUNCTION WITH RADIOLOGIST-ASSISTED MACHINE LEARNING
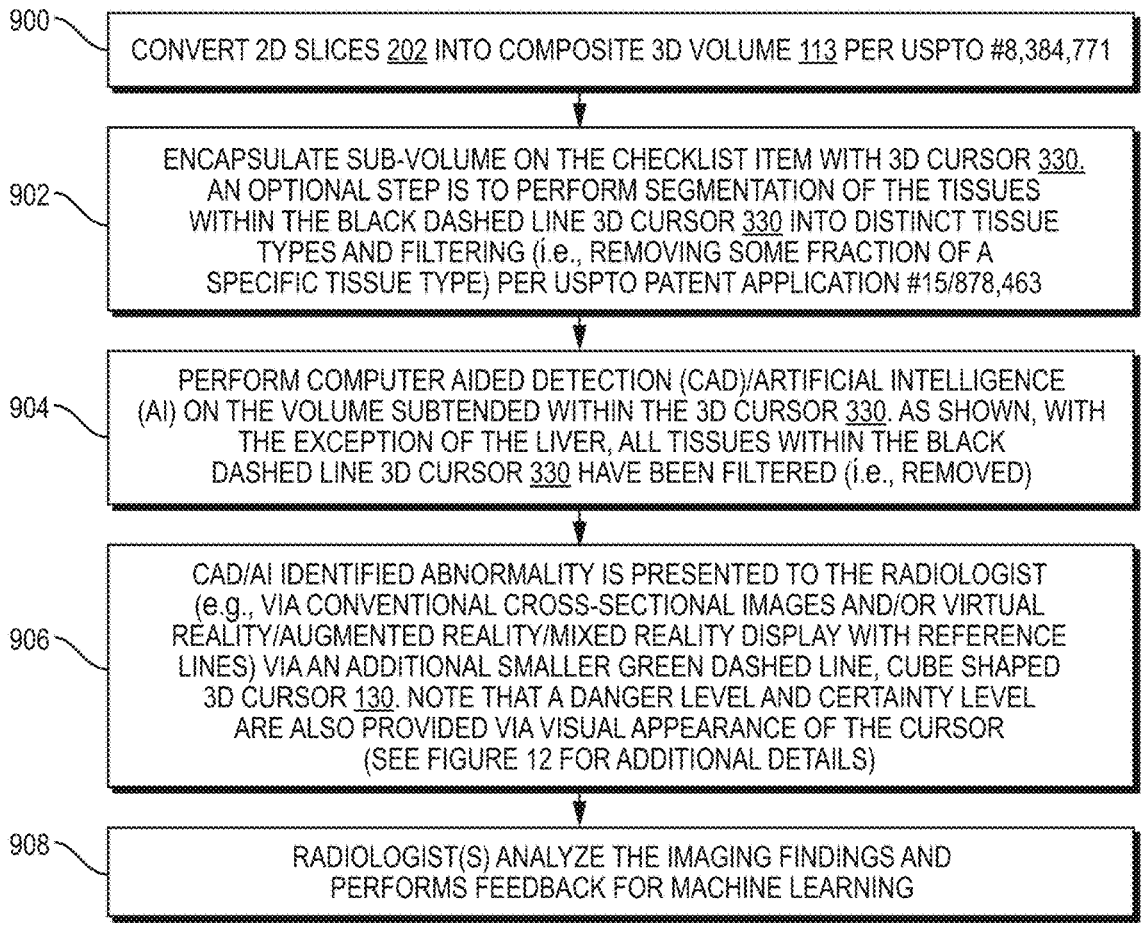
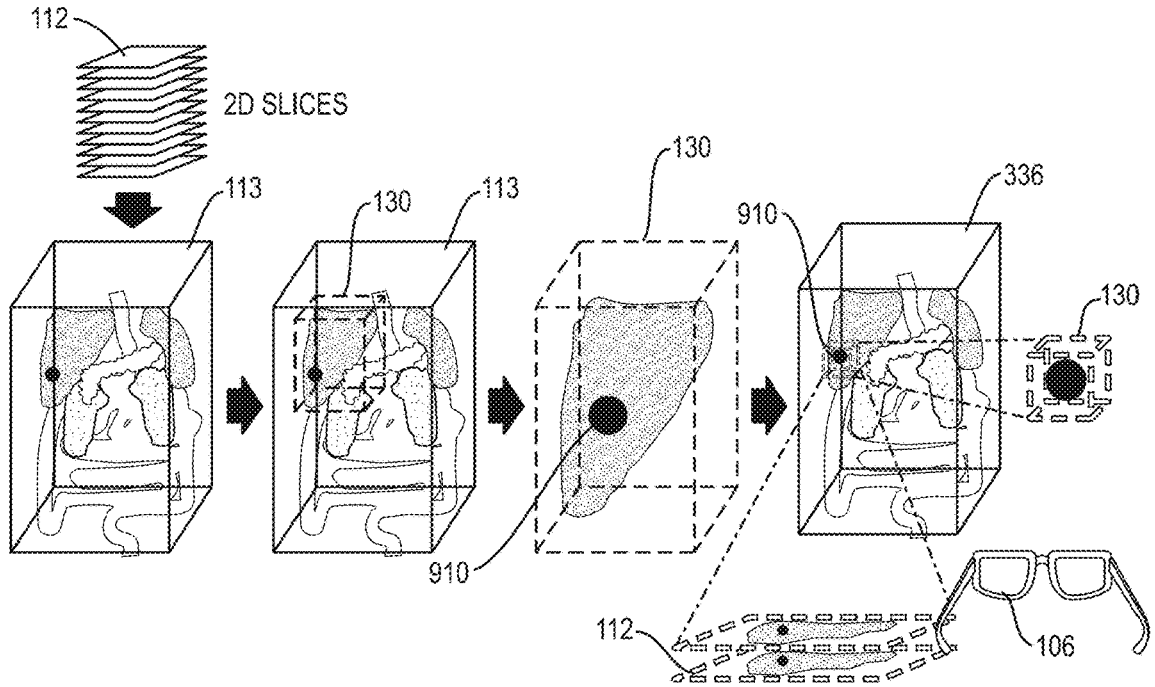
FIG. 9

ILLUSTRATION OF THE RELATIONSHIP BETWEEN THE COMPOSITE
VOLUME, A SUB-VOLUME AND VOLUME SUBTENDING 3D CURSOR

ILLUSTRATION OF THE RADIOLOGIST'S WORKSTATION
WITH A VIRTUAL BUCKET
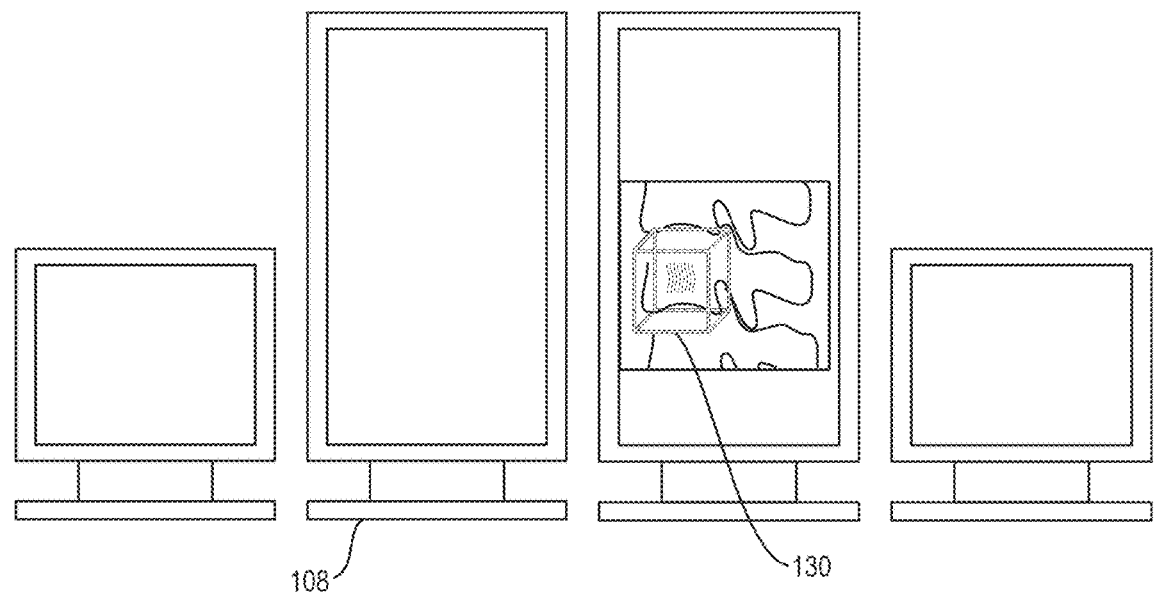
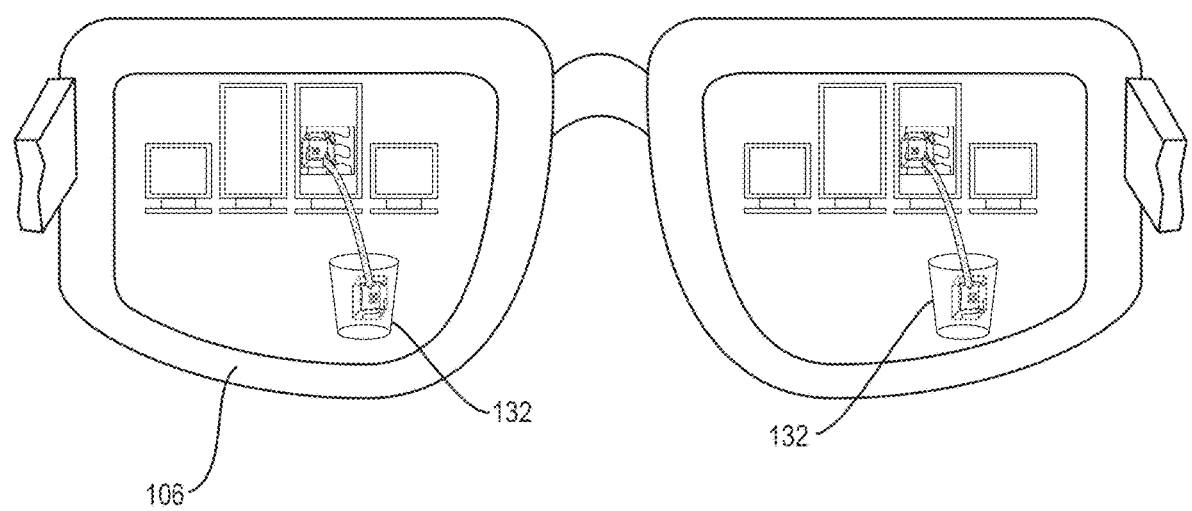
FIG. 11

ILLUSTRATION OF RADIOLOGY REPORT INCORPORATING 3D CURSORS AND RADIOLOGIST-ASSISTED MACHINE LEARNING REPORTING TECHNIQUE

Exam: CT Abdomen/Pelvis
Patient Name: #########
Date of Birth: #########
Medical Record Number: #########
Accession Number: #########
Indication for exam: Acute right flank pain
AI identified history: Microhematuria
Comparisons: None
Technique: Noncontrast CT scan of the abdomen and pelvis was performed.
Radiation Dose: #####
Findings:

| | |
|---|---|
| Lungs: | Negative |
| Heart: | Negative |
| Liver: | Positive |
| Gallbladder: | Negative |
| Spleen: | Negative |
| Pancreas: | Negative |
| Adrenal glands: | Negative |
| Kidneys: | Negative |
| Ureters: | Positive |
| Bladder: | Negative |
| Esophagus: | Negative |
| Stomach: | Negative |
| Small bowel: | Negative |
| Colon: | Negative |
| Rectum: | Negative |
| Vasculature: | Negative |
| Lymph nodes: | Negative |
| Bones: | Negative |
| Muscles: | Negative |
| Subcutaneous fat: | Negative |

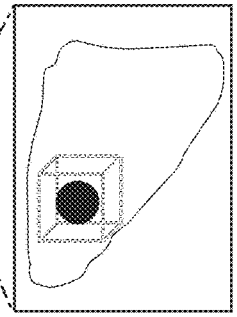

For this finding, the radiologist agreed with AI diagnosis, management and imaging recommendations. There is a 1 cm spherical, fluid-density lesion located in the liver, most likely representing a simple cyst. This is an incidental, benign finding and no management action or follow up is required.

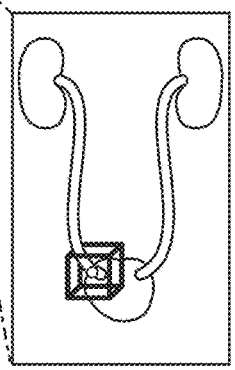

For this finding, the radiologist agreed with AI diagnosis, management and imaging recommendations. A calcified stone measuring 0.3 is located in the distal ureter 1 cm proximal to the ureterovesicular junction. No hydroureteronephrosis. Recommend urology consultation and follow up CT Abdomen/Pelvis exam as needed.

Impression:
A calcified stone measuring 0.3 is located in the distal ureter 1 cm proximal to the ureterovesicular junction. No hydroureteronephrosis. Recommend urology consultation and follow up CT Abdomen/Pelvis exam as needed.

FIG. 15

RADIOLOGIST ASSISTED MACHINE LEARNING

CROSS REFERENCES TO RELATED APPLICATIONS

This patent application is a continuation of U.S. patent application Ser. No. 16/939,192 filed on Jul. 27, 2020, which is a continuation in part of U.S. patent application Ser. No. 16/843,988 filed on 2020 Apr. 9, which is a continuation of U.S. Pat. No. 10,586,400 (U.S. patent application Ser. No. 15/904,092 filed on 2018 Feb. 23) issued on 2020 Mar. 10 and U.S. Pat. No. 10,657,731 (U.S. patent application Ser. No. 16/752,662 filed on 2020 Jan. 26) issued on 2020 May 19. This patent application is also a continuation in part of U.S. patent application Ser. No. 16/195,251 filed on 2018 Nov. 19, which claims the benefit of U.S. Provisional Application No. 62/651,934 filed on 2018 Apr. 3, U.S. Provisional Application No. 62/695,868 filed on Jul. 10, 2019 and U.S. Provisional Application No. 62/628,527 filed on Feb. 9, 2018. This patent application is also claims the benefit of PCT/US2019/023968 filed on 2019 Mar. 26, which claims the benefit of U.S. Provisional Patent Application No. 62/651,934 filed on 2018 Apr. 3 and U.S. Provisional Patent Application No. 62/748,555 filed on 2018 Oct. 22.

TECHNICAL FIELD

Aspects of this disclosure are generally related to use of computer aided detection (CAD) and artificial intelligence (AI) in the medical field, and more particularly to machine learning in diagnostic radiology.

BACKGROUND

AI and CAD are quickly changing the field of medical imaging. As an example, many mammographers use CAD to help detect breast cancer on 2D imaging. However, CAD systems have limitations including lack of optimization for clinical impact and lack of quantification of performance efficiency.

SUMMARY

All examples, aspects and features mentioned in this document can be combined in any technically conceivable way.

In accordance with an aspect a method comprises: continuously updating a training dataset while analyzing medical image data with a medical image diagnostic computer having machine-learning capability, comprising the steps of: using a three-dimensional cursor to select a sub-volume of a medical image, wherein the selected sub-volume corresponds to an item on a diagnostic checklist; analyzing the selected sub-volume to create a human-generated analysis; and using the human-generated analysis to update the training dataset. Some implementations comprise analyzing the selected sub-volume using the training dataset to create a machine-generated analysis with the diagnostic computer before manually analyzing the selected sub-volume. Some implementations comprise resolving disagreement between the human-generated analysis and the machine-generated analysis before using the human-generated analysis to update the training dataset. Some implementations comprise generating a computer-made explanation for the machine-generated analysis. Some implementations comprise updating the human-generated analysis based on the explanation before using the human-generated analysis to update the training dataset. Some implementations comprise prompting a consensus review of the human-generated analysis and machine-generated analysis. Some implementations comprise updating the human-generated analysis based on the consensus review before using the human-generated analysis to update the training dataset. Some implementations comprise the diagnostic computer retrieving and presenting patient-specific data pertinent to the item on the checklist to facilitate creation of the human-generated analysis. In some implementations creating the human-generated analysis comprises creating at least one of: terminology describing findings or diagnosis; marked pixels or voxels; and an indication of certainty of the findings or diagnosis. In some implementations creating the machine-generated analysis comprises creating at least one of: terminology describing findings or diagnosis; marked pixels or voxels; and an indication of certainty of the findings or diagnosis. Some implementations comprise performing segmentation on tissue within the selected sub-volume. Some implementations comprise filtering out tissue within the selected sub-volume that is not associated with a finding. Some implementations comprise automatically re-sizing the three-dimensional cursor to encompass tissue associated with the finding. In some implementations the checklist comprises multiple items, each of which is analyzed, and the method comprises generating a report based on the human-generated analysis. Some implementations comprise including an indication of disagreement between the human-generated analysis and the machine-generated analysis. Some implementations comprise the three-dimensional cursor visually indicating confidence or dangerousness of a diagnosis. Some implementations comprise placing tissue associated with a finding in a virtual container. Some implementations comprise selecting a virtual container from a normal finding container, a disease-specific container, and differential diagnosis container.

In accordance with an aspect an apparatus comprises: a medical image diagnostic computer having machine-learning capability, the diagnostic computer comprising a non-transitory medium on which is stored computer program logic that continuously updates a training dataset while analyzing medical image data with, comprising: item selection logic that selects a sub-volume of a medical image with a three-dimensional cursor, wherein the selected sub-volume corresponds to an item on a diagnostic checklist; input logic that receives input that creates a human-generated analysis of the selected sub-volume; and update logic that updates the training dataset based on the human-generated analysis. Some implementations comprise diagnostic logic that analyzes the selected sub-volume using the training dataset to create a machine-generated analysis before the human-generated analysis is generated. Some implementations comprise resolution logic that resolves disagreement between the human-generated analysis and the machine-generated analysis before the human-generated analysis is used to update the training dataset. Some implementations comprise virtual guru logic that generates a computer-made explanation for the machine-generated analysis. In some implementations the resolution logic updates the human-generated analysis based on the explanation before using the human-generated analysis to update the training dataset. In some implementations the resolution logic prompts a consensus review of the human-generated analysis and machine-generated analysis. In some implementations the resolution logic updates the human-generated analysis based on the consensus review before using the human-generated analysis to update the training dataset. Some implementations comprise the diagnostic computer retrieving and presenting patient-specific data pertinent to the item on the checklist to facilitate creation of the human-generated analysis. In some implementations the human-generated analysis comprises at least one of: terminology describing findings or diagnosis; marked pixels or voxels; and an indication of certainty of the findings or diagnosis. In some implementations the machine-generated analysis comprises at least one of: terminology describing findings or diagnosis; marked pixels or voxels; and an indication of certainty of the findings or diagnosis. Some implementations comprise segmentation logic that segments tissue within the selected sub-volume. Some implementations comprise filtering logic that removes from an image tissue within the selected sub-volume that is not associated with a finding. Some implementations comprise logic that re-sizes the three-dimensional cursor to encompass tissue associated with the finding. In some implementations the checklist comprises multiple items, each of which is analyzed, and the method comprises logic that generates a report based on the human-generated analysis. In some implementations the logic that generates the report includes an indication of disagreement between the human-generated analysis and the machine-generated analysis in the report. Some implementations comprise the three-dimensional cursor visually indicating confidence or dangerousness of a diagnosis. Some implementations comprise a virtual container in which tissue associated with a finding is placed. In some implementations the virtual container is selected from a normal finding container, a disease-specific container, and differential diagnosis container.

BRIEF DESCRIPTION OF THE FIGURES

FIG. 9 provides a flow diagram and illustration for using the 3D cursor in conjunction with radiologist-assisted machine learning.

FIG. 11 illustrates the radiologist's workstation without (top) and looking through (bottom) an augmented reality headset where the radiologist can see the virtual bucket only when looking through the augmented reality (AR) display.

FIG. 15 illustrates an example radiology report incorporating the 3D cursor and radiologist-assisted machine learning reporting technique.

DETAILED DESCRIPTION

Some aspects, features and implementations described herein may include machines such as computers, electronic components, optical components, and processes such as computer-implemented steps. It will be apparent to those of ordinary skill in the art that the computer-implemented steps may be stored as computer-executable instructions on a non-transitory computer-readable medium. Furthermore, it will be understood by those of ordinary skill in the art that the computer-executable instructions may be executed on a variety of tangible processor devices. For ease of exposition, not every step, device or component that may be part of a computer or data storage system is described herein. Those of ordinary skill in the art will recognize such steps, devices and components in view of the teachings of the present disclosure and the knowledge generally available to those of ordinary skill in the art. The corresponding machines and processes are therefore enabled and within the scope of the disclosure.

The terminology used in this disclosure is intended to be interpreted broadly within the limits of subject matter eligibility. The terms "logical" and "virtual" are used to refer to features that are abstractions of other features, e.g. and without limitation abstractions of tangible features. The term "physical" is used to refer to tangible features. For example, multiple virtual computing devices could operate simultaneously on one physical computing device. The term "logic" is used to refer to special purpose physical circuit elements and software instructions that are stored on a non-transitory computer-readable medium and implemented by multi-purpose tangible processors. Furthermore, the terminology "3D cursor" is meant to refer to a type of cursor that subtends a volume. The terminology "sub-volume" may be used to in conjunction with 3D cursor to indicate that the volume within the 3D cursor represents only a fraction of the volume in the entire medical image (e.g., liver is contained in a 3D cursor, or sub-volume, of the entire abdomen and pelvis CT scan imaging volume).

U.S. Provisional Patent Application 62/748,555 titled A METHOD AND APPARATUS FOR RADIOLOGIST ASSISTED MACHINE LEARNING, filed Oct. 22, 2018 is incorporated by reference. U.S. Provisional Patent Application 62/651,934 titled A METHOD TO OPTIMIZE THE INTERACTION BETWEEN A RADIOLOGIST AND ARTIFICIAL INTELLIGENCE COMPUTER SYSTEM THROUGH INTERACTIVE, VOLUME-SUBTENDING 3D CURSOR USE TO IMPROVE DIAGNOSTIC ACCURACY, filed Apr. 3, 2018 is incorporated by reference.

Figure 1:
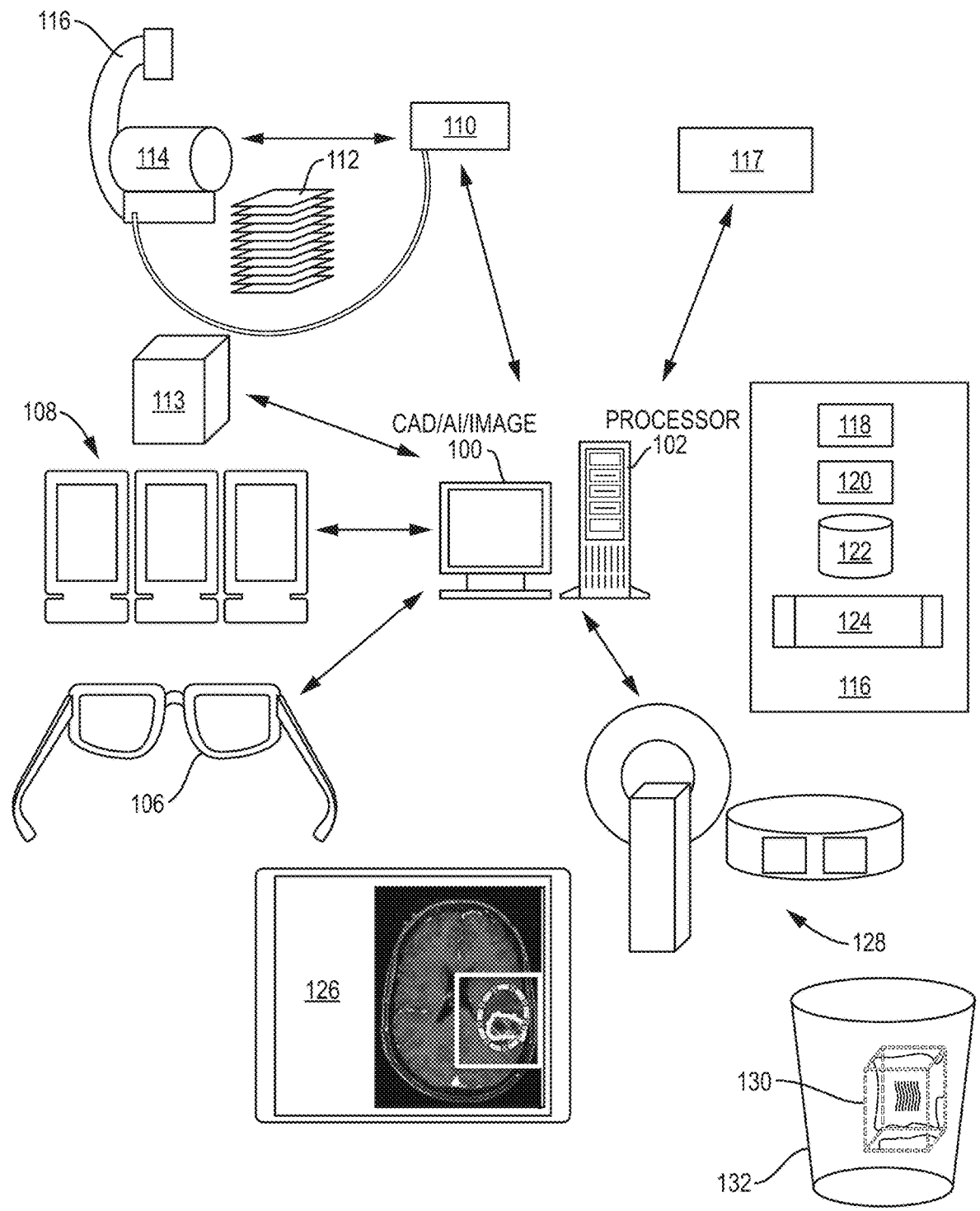
FIG. 1 illustrates the key components for an integrated radiologist-assisted machine learning process.

FIG. 1 illustrates an imaging and diagnostic system associated with radiologist-assisted machine learning capabilities. In general, machine learning enables a computer to progressively improve performance of a task without being explicitly programmed to perform every aspect of that task. CAD and/or AI programs 100 running on an image processing and diagnostic computer 102 partially automate medical diagnostics and learn from radiologist review. The system includes external devices such as a controller 104 and a headset 106. An IO device 108 includes a viewing station with multiple 2D monitors. Communications linkages may include a link between any of the above elements, such as a link between the controller and the image processing and diagnostic computer, a link between the image processing and diagnostic computer and the headset; and a links between the image processing and diagnostic computer, a Picture Archiving Communications System (PACS) system 110 which can display cross-sectional images 112. Images can be processed to form a 3D volume 113 in accordance with U.S. Pat. No. 8,384,771. Patient medical records 117 can also be displayed on the monitors. Also running as programs on the image processing and diagnostic computer 116 are an image processing system as disclosed in U.S. patent application Ser. No. 15/904,092 for PROCESSING 3D MEDICAL IMAGES TO ENHANCE VISUALIZATION, filed Feb. 23, 2018, which is incorporated by reference, for 3D image generation and image manipulation based on commands from the controller, a report generator, and AI for data extraction from PACS and patient's medical records, which may include responses to a questionnaire. The 2D medical images 112 of an anatomic structure 114 of interest are generated. Imaging capabilities 116 may include x-ray, ultrasound, mammogram, computed tomography, magnetic resonance imaging, positron emission tomography, single photon emission computed tomography, or tomosynthesis, for example and without limitation. The 2D medical images 112 are provided to the image processing and diagnostic computer 100, that includes processors 118 (e.g., CPUs and GPUs), volatile memory 120 (e.g., RAM), and non-volatile storage 122 (e.g. HDDs and SSDs). A program 124 running on the image processor implements one or more of the steps described in this patent to accomplish radiologist-assisted machine learning (RAML). The medical images are displayed on an IO device 126 and marked up by the radiologist. The IO device may include a virtual or augmented reality headset 106, monitor, tablet computer, PDA (personal digital assistant), mobile phone, or any of a wide variety of devices, either alone or in combination. The TO device may include a touchscreen and may accept input from external devices (represented by 128) such as a keyboard, mouse, and any of a wide variety of equipment for receiving various inputs. Finally, a series of virtual objects including interactive volume-subtending 3D cursors 130 and virtual buckets 132 will also be integral to this system.

Figure 2:
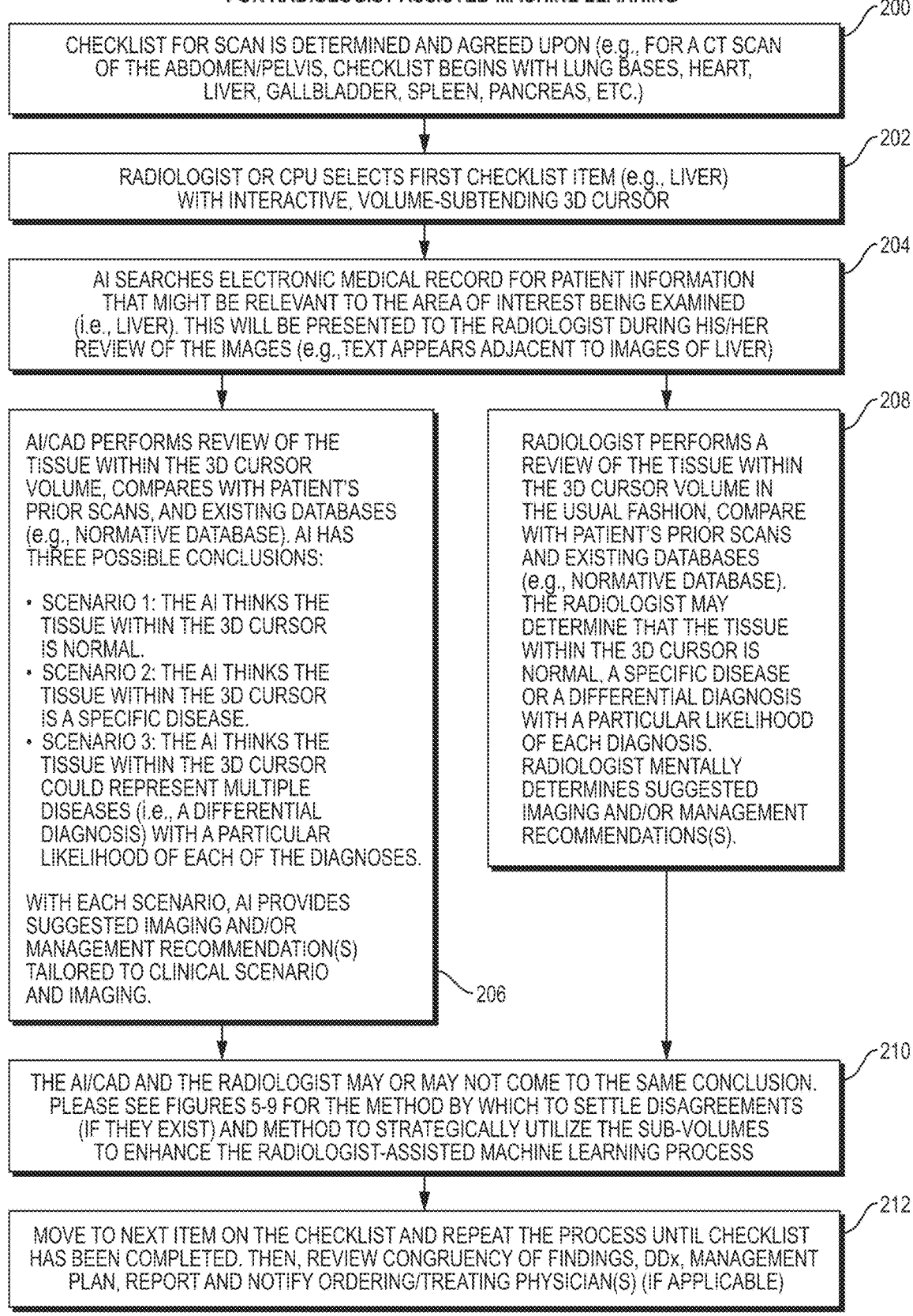
FIG. 2 is a generalized flow diagram that illustrates a checklist-based volume-by-volume 3D cursor approach for radiologist-assisted machine learning.

FIG. 2 is a generalized flow diagram that illustrates a checklist-based volume-by-volume 3D cursor approach for radiologist-assisted machine learning. Preparatory steps may include downloading cases for review from a PACS and creating a 3D volume from a set of 2D image slices as outlined in U.S. Pat. No. 8,384,771. An additional preparatory step may include performing segmentation of the imaged tissues into discrete tissue types. As indicated in step 200, the radiologist (or other physician) follows a checklist of key body parts which are reviewed in a sequential fashion. For example, for a CT scan of the abdomen/pelvis, the checklist may include lung bases, heart, liver, gallbladder, spleen, pancreas, etc. As indicated in step 202, the radiologist or CPU selects first checklist item (e.g., liver) with interactive, volume-subtending 3D cursor. As indicated in step 204, the AI searches electronic medical record for patient information that might be relevant to the area of interest being examined (i.e., liver). This will be presented to the radiologist during his/her review of the images (e.g., text appears adjacent to images of liver). For example, important information may include the most recent liver function tests during the review of the liver. As indicated in step 206, the volume within the 3D cursor is analyzed by the AI and/or CAD algorithm. The algorithm compares with the patient's prior scans and existing databases. AI has three possible conclusions. First, AI may determine that the tissue within the 3D cursor is normal. Second, the AI may determine that the tissue within the 3D cursor is a specific disease. Third, the AI may determine that the tissue within the 3D cursor could represent multiple diseases (i.e., a differential diagnosis) with a particular likelihood of each of the diagnoses. With each scenario, AI provides suggested imaging and/or management recommendation(s) tailored to clinical scenario and imaging. In a concurrent fashion, the radiologist performs a review 208 of the tissue within the 3D cursor volume in this usual fashion or using advanced visualization techniques. He/she will compare with the patient's prior scans and existing databases as well. The radiologist may determine that the tissue within the 3D cursor is normal, a specific disease or a differential diagnosis with a particular likelihood of each diagnosis. The radiologist mentally determines suggested imaging and/or management recommendation(s). As indicated in step 210, the AI/CAD and the radiologist may or may not come to the same conclusion. Please see FIGS. 3-7 for the method by which to settle disagreements (if they exist) and method to strategically utilize the sub-volumes to enhance the radiologist-assisted machine learning process. As indicated in step 212, the radiologist will move to next item on the checklist and repeat the process until checklist has been completed. Then, review congruency of findings, DDx, management plan, report and notify ordering/treating physician(s) (if applicable).

Figure 3:
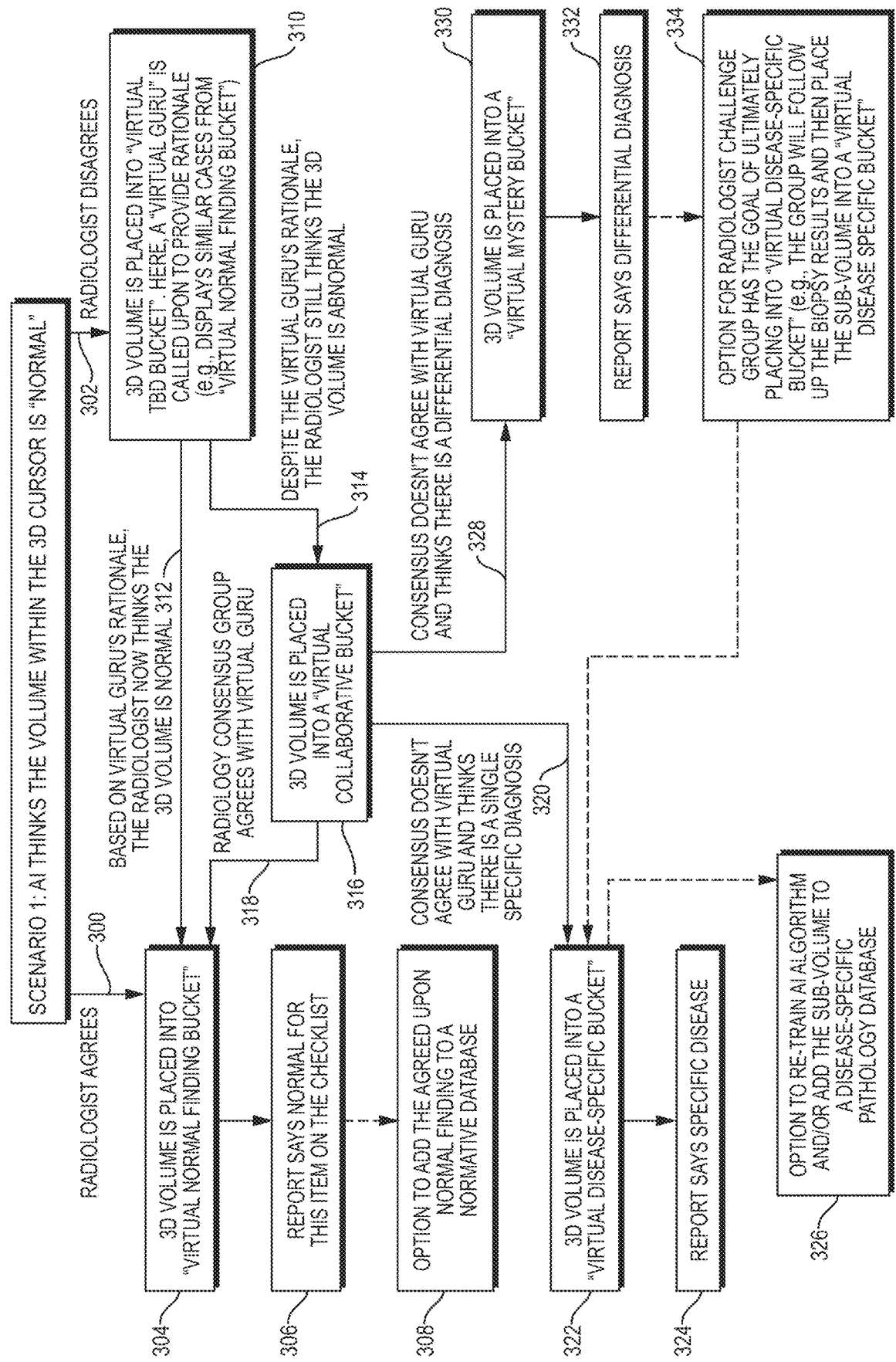
FIG. 3 illustrates a flow diagram for radiologist-assisted machine learning for the scenario wherein the AI concludes that the volume within the 3D cursor is "normal".

FIG. 3 illustrates a flow diagram for radiologist-assisted machine learning for the scenario wherein the AI concludes that the volume within the 3D cursor is "normal". As indicated in 300, the radiologist may agree with the AI's conclusion that the volume within the 3D cursor is normal. If the radiologist agrees, the 3D volume can be placed into a "virtual normal finding bucket" 304. The radiology report will state that this item on the checklist is normal 306. The radiologist has the option to add the agreed upon normal finding to a normative database 308. However, the radiologist may also disagree with the AI 302. In this case, the 3D volume is placed into "virtual TBD bucket" 310. Here, a "virtual guru" is called upon to provide rationale (e.g., displays similar cases from virtual normal finding bucket"). If, based on the virtual guru's rationale, the radiologist now thinks the volume within the 3D cursor is normal 312, the radiologist places the 3D volume into a "virtual normal finding bucket" 304. If despite the virtual guru's explanation, the radiologist still thinks the volume within the 3D cursor is abnormal 314, he/she places the volume within the 3D cursor into a "virtual collaborative bucket" 316. At this juncture, the interpreting radiologist collaborates with other radiologist to evaluate the suspected abnormality within 3D cursor. This could be in the form of a formal radiology conference or informal "curbside" radiologist-to-radiologist consult. If the radiology consensus agrees with the virtual guru that the volume within the 3D cursor is normal 318, the volume is placed into the "virtual normal finding bucket" 304. If the radiology consensus doesn't agree with the virtual guru and believes that there is a single specific diagnosis 320, then the 3D volume is placed into a "virtual disease-specific bucket" 322. Then, the report will discuss the specific disease (or pathology entity) 324. Additional options include retraining the AI algorithm and/or adding the 3D volume to a disease specific pathology database 326. If the radiology consensus doesn't agree with the virtual guru and thinks that instead of the volume within the 3D cursor being normal, there is an abnormality with a differential diagnosis 328. The 3D volume is placed into a "virtual mystery bucket" 330. The report states the differential diagnosis with the specified order as determined by the radiologist and radiologist's consensus group 332. Then, there is an option for the radiologist challenge group with the goal of ultimately placing the 3D volume into a "virtual disease specific bucket" 334. For example, the group will follow up the biopsy results and then place the sub-volume into a "virtual disease specific bucket" 322.

Figure 4:
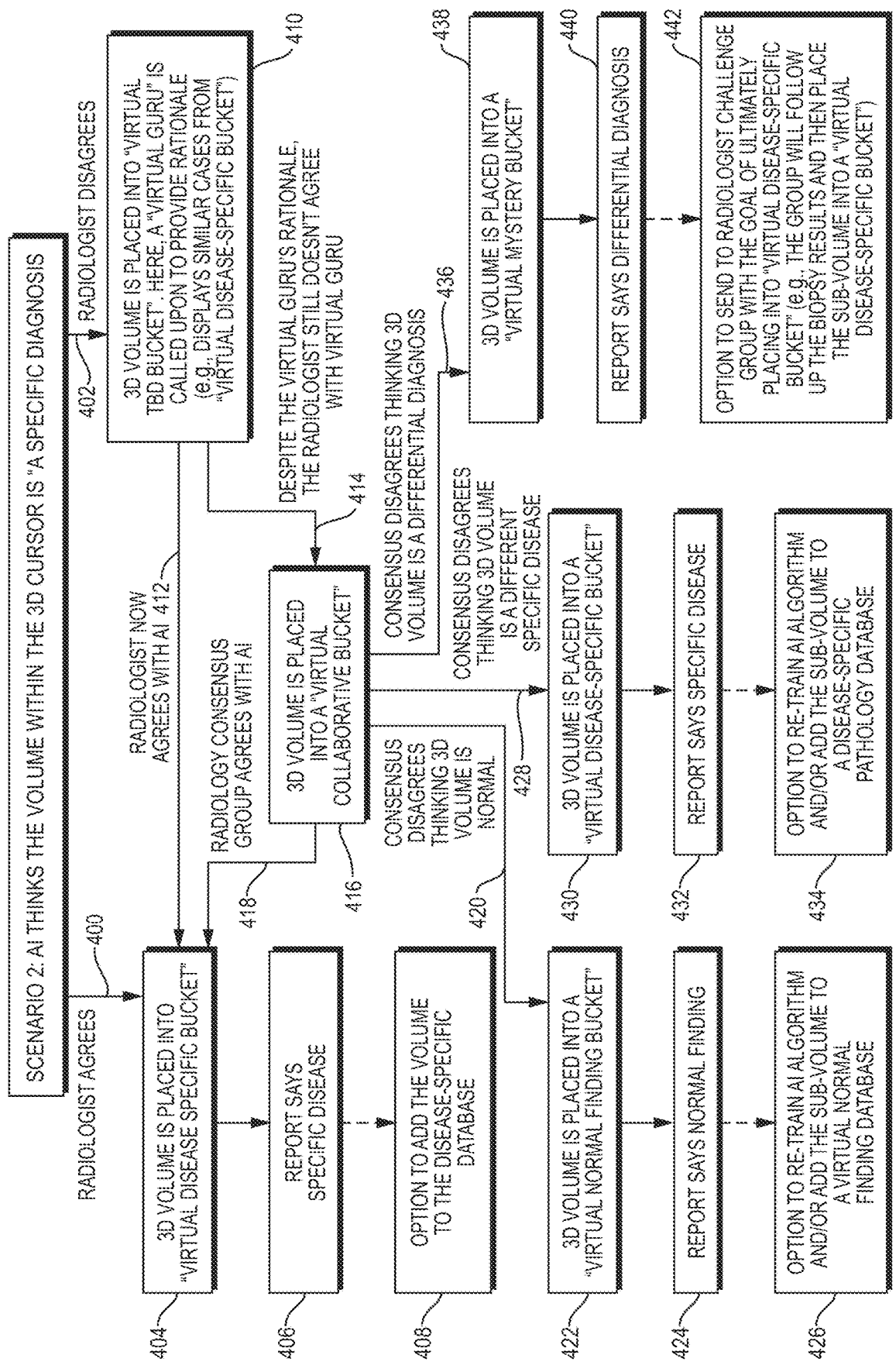
FIG. 4 illustrates a flow diagram for radiologist-assisted machine learning for the scenario wherein the AI concludes that the volume within the 3D cursor is a "specific diagnosis".

FIG. 4 illustrates a flow diagram for radiologist-assisted machine learning for the scenario wherein the AI concludes that the volume within the 3D cursor is a "specific disease". As indicated in 400, the radiologist may agree with the AI's conclusion that the volume within the 3D cursor is the said specific disease. If the radiologist agrees, the 3D volume can be placed into a "virtual disease specific bucket" 404. The radiology report will describe the specific disease 406. Please note that AI processes should also have the ability to accurately describe the both normal anatomy and pathology. Feedbacks similar to those designed in this patent through the use of 3D cursors and "virtual buckets" can also be used to improve descriptions performed by AI. The radiologist has the option to add the agreed upon 3D volume to a disease specific database 408. However, the radiologist may also disagree with the AI 402. In this case, the 3D volume is placed into "virtual TBD bucket" 410. Here, a "virtual guru" is called upon to provide rationale (e.g., displays similar cases from virtual disease specific bucket"). If, based on the virtual guru's rationale, the radiologist now thinks the volume within the 3D cursor represents the said specific disease 412, the radiologist places the 3D volume into a "virtual disease specific bucket" 404. If despite the virtual guru's explanation, the radiologist still doesn't agree with the virtual guru 414, he/she places the volume within the 3D cursor into a "virtual collaborative bucket" 416. At this juncture, the interpreting radiologist collaborates with other radiologist to evaluate the 3D volume. This could be in the form of a formal radiology conference or informal "curbside" radiologist-to-radiologist consult. If the radiology consensus agrees with the virtual guru that the volume within the 3D cursor is the said specific disease 418, the volume is placed into the "virtual disease specific bucket" 404. If the radiology consensus doesn't agree with the virtual guru and believes that the 3D volume is normal 420, then the 3D volume is placed into a "virtual normal finding bucket" 422. Then, the report will state that that item on the checklist is normal 424. Options include re-training the AI algorithm and/or adding the sub-volume to a "virtual normal finding bucket" 426. If the radiology consensus doesn't agree with the virtual guru and believes that the 3D volume is a specific disease 428, then the 3D volume is placed into a "virtual specific disease bucket" 430. Then, the report will state the specific disease 432. Options include re-training the AI algorithm and/or adding the 3D cursor volume to a disease specific pathology database 434. Finally, the radiology consensus group may disagree with the virtual guru and believe that the volume within the 3D cursor could be a differential diagnosis. In this case, the 3D volume is placed into a "virtual mystery bucket" 438. The report states the differential diagnosis with the likelihood of each diagnosis discussed 440. Options include sending the 3D cursor to a radiology challenge group with the goal of ultimately placing into "virtual disease-specific bucket" (e.g., the group will follow up the biopsy results and then place the sub-volume into a "virtual disease specific bucket" 430). Options include sending both the sub-volume of diagnostic question and the total imaging volume to the radiology challenge group.

Figure 5:
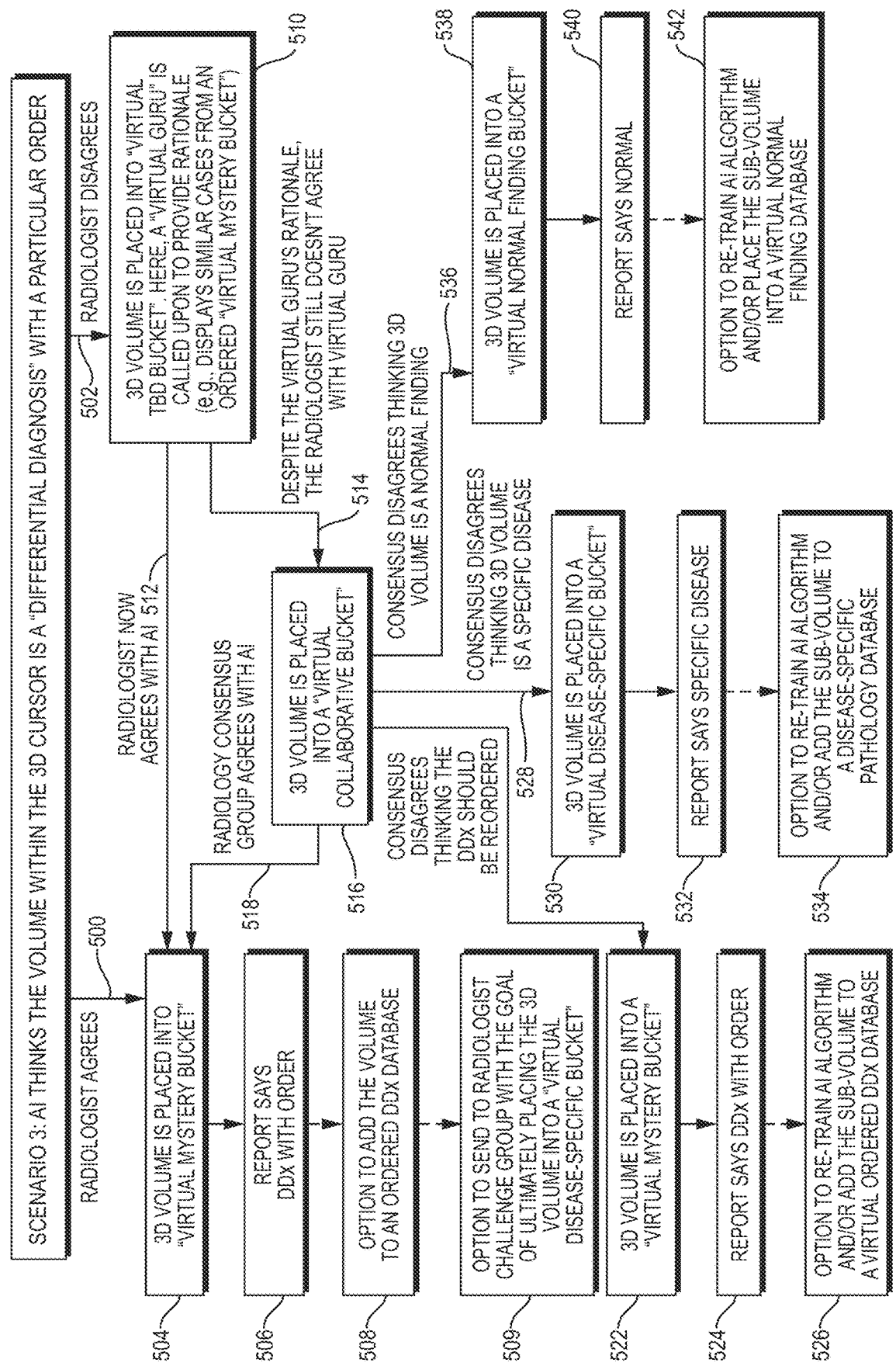
FIG. 5 illustrates a flow diagram for radiologist-assisted machine learning for the scenario wherein the AI concludes that the volume within the 3D cursor is a "differential diagnosis" with a likelihood of each diagnosis.

FIG. 5 illustrates a flow diagram for radiologist-assisted machine learning for the scenario wherein the AI concludes that the volume within the 3D cursor is a "differential diagnosis of multiple possible diseases" with a particular likelihood of each disease. As indicated in 500, the radiologist may agree with the AI's conclusion that the volume within the 3D cursor is the said differential diagnosis. If the radiologist agrees, the 3D volume can be placed into a "virtual mystery bucket" 504. The radiology report will describe the differential diagnosis 506 with the particular order. Please note that AI processes should also have the ability to accurately describe the imaging findings both normal anatomy and pathology. Furthermore, the AI system should be able to use imaging terminology as to why one differential diagnosis is favored over another differential diagnosis. Feedbacks similar to those designed in this patent through the use of 3D cursors and "virtual buckets" can also be used to improve descriptions performed by AI. The radiologist has the option to add the agreed upon 3D volume to a differential diagnosis (DDx) database 508. An additional option is to send the sub-volume in question with or without the total imaging volume to a radiologist challenge group wherein the challenge group has the goal of ultimately placing the 3D volume into a "virtual disease specific bucket." However, the radiologist may also disagree with the AI 502. In this case, the 3D volume is placed into "virtual TBD bucket" 510. Here, a "virtual guru" is called upon to provide rationale (e.g., displays similar cases from "virtual mystery bucket"). If, based on the virtual guru's rationale, the radiologist now thinks the volume within the 3D cursor represents the said differential diagnosis including the order of the differential diagnosis 512, the radiologist places the 3D volume into a "virtual mystery bucket" 504. If despite the virtual guru's explanation, the radiologist still doesn't agree with the virtual guru 514, he/she places the volume within the 3D cursor into a "virtual collaborative bucket"

516. At this juncture, the interpreting radiologist collaborates with other radiologist to evaluate the 3D volume. This could be in the form of a formal radiology conference or informal "curbside" radiologist-to-radiologist consult. If the radiology consensus group agrees with the virtual guru that the volume within the 3D cursor is the said differential diagnosis with the agreed likelihood of the differential diagnoses 518, the volume is placed into the "virtual mystery bucket" 504. The radiology consensus group may also disagree with the virtual guru and believe that the volume within the 3D cursor could be a differential diagnosis (different order, different set of diagnoses or combination thereof). In this case, the 3D volume is placed into a different "virtual mystery bucket" 522. The report states the differential diagnosis with the likelihood of each diagnosis discussed 524. An option 526 is to re-train the AI algorithm, add the 3D cursor to a differential diagnosis database and/or send the sub-volume (with or without the entire imaging volume and clinical data elements to a radiology challenge group with the goal of ultimately placing into "virtual disease-specific bucket" (e.g., the group will follow up the biopsy results and then place the sub-volume into a "virtual disease specific bucket" 530). Options include sending both the sub-volume of diagnostic question and the total imaging volume to the radiology challenge group. Finally, if the radiology consensus doesn't agree with the virtual guru and believes that the 3D volume is normal 536, then the 3D volume is placed into a "virtual normal finding bucket" 538. Then, the report will state that that item on the checklist is normal 540. Options include re-training the AI algorithm and/or adding the sub-volume to a virtual normal finding database 542.

Figure 6:
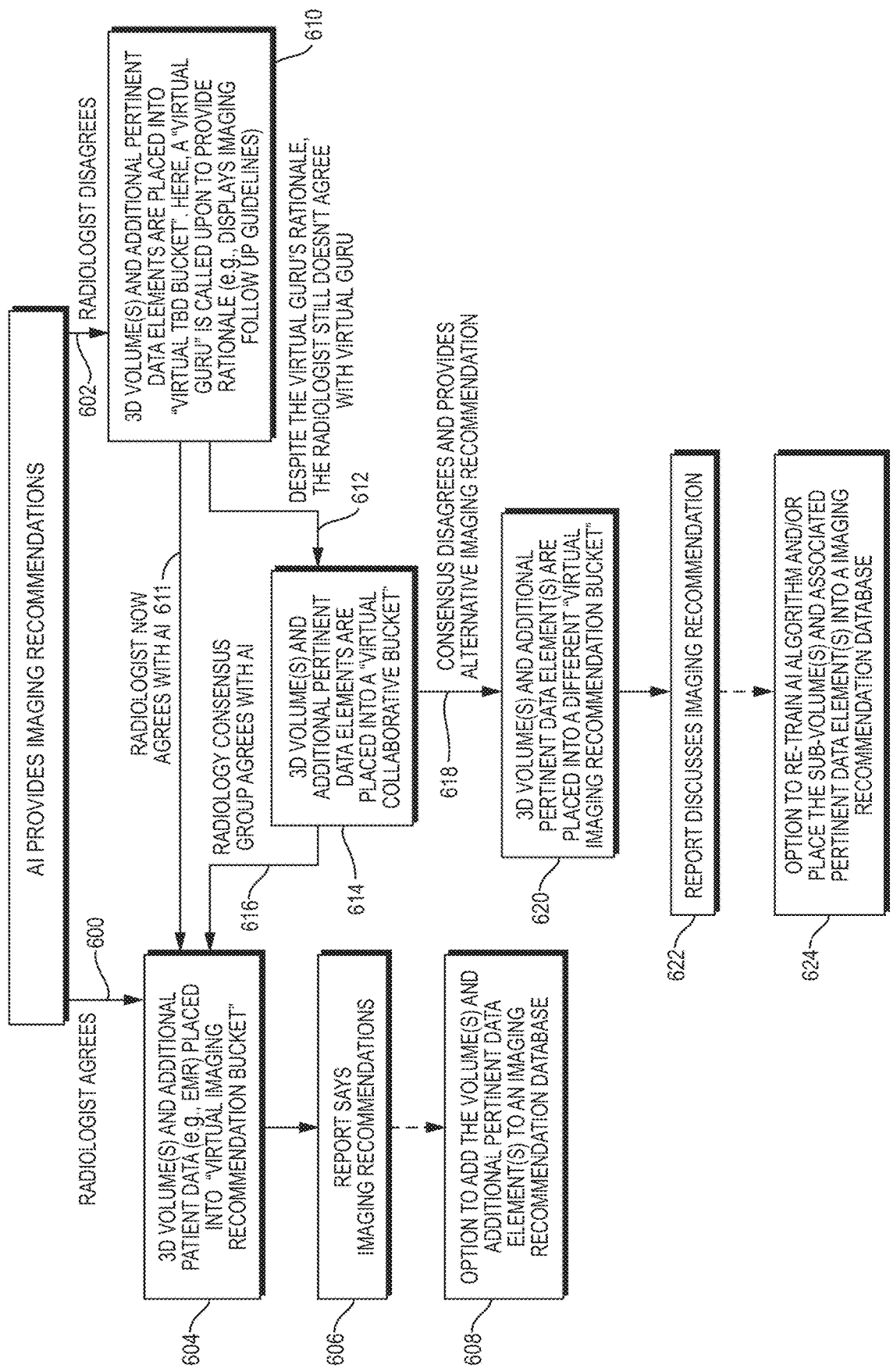
FIG. 6 illustrates a flow diagram for radiologist-assisted machine learning for the scenario wherein the AI reviews the examination and provides further imaging recommendations.

FIG. 6 illustrates a flow diagram for radiologist-assisted machine learning for the scenario wherein the AI reviews the examination and provides further imaging recommendations. If the radiologist agrees with the AI 600, then the 3D volume(s) and additional pertinent data (e.g., data from the Electronic Medical Record (EMR)) are together placed into the "virtual imaging recommendation bucket" 604. The radiology report states the imaging recommendation 606. Then, an option is to add the volume and additional pertinent data element(s) to an imaging recommendation database 608. If the radiologist disagrees with the AI 602, then the 3D volume(s) and additional pertinent data elements are placed into "virtual TBD (To Be Determined) bucket" 610. Here, a "virtual guru" is called upon to provide rationale (e.g., displays imaging follow up guidelines). If the radiologist now agrees with the AI 611, then the 3D volume(s) and additional pertinent data element(s) are added to the "virtual imaging recommendation bucket" 604. If, despite the virtual guru's rationale, the radiologist still doesn't agree with the virtual guru 612, then the 3D volume(s) and additional pertinent data element(s) are placed into a "virtual collaborative bucket" 614. If the radiology consensus group agrees with the AI 616, then the 3D volume(s) and additional pertinent data element(s) are added to the virtual imaging recommendation bucket" 604. If the radiology consensus group disagrees and believes an alternative imaging recommendation is warranted 618, then the 3D volume(s) and additional pertinent data element(s) are placed into a different "virtual imaging recommendation bucket" 620. Then, the radiology report discusses the imaging recommendations 622. An option at this juncture is to re-train the AI algorithm and/or place the sub-volume(s) and associated pertinent data element(s) into a imaging recommendation database 624.

Figure 7:
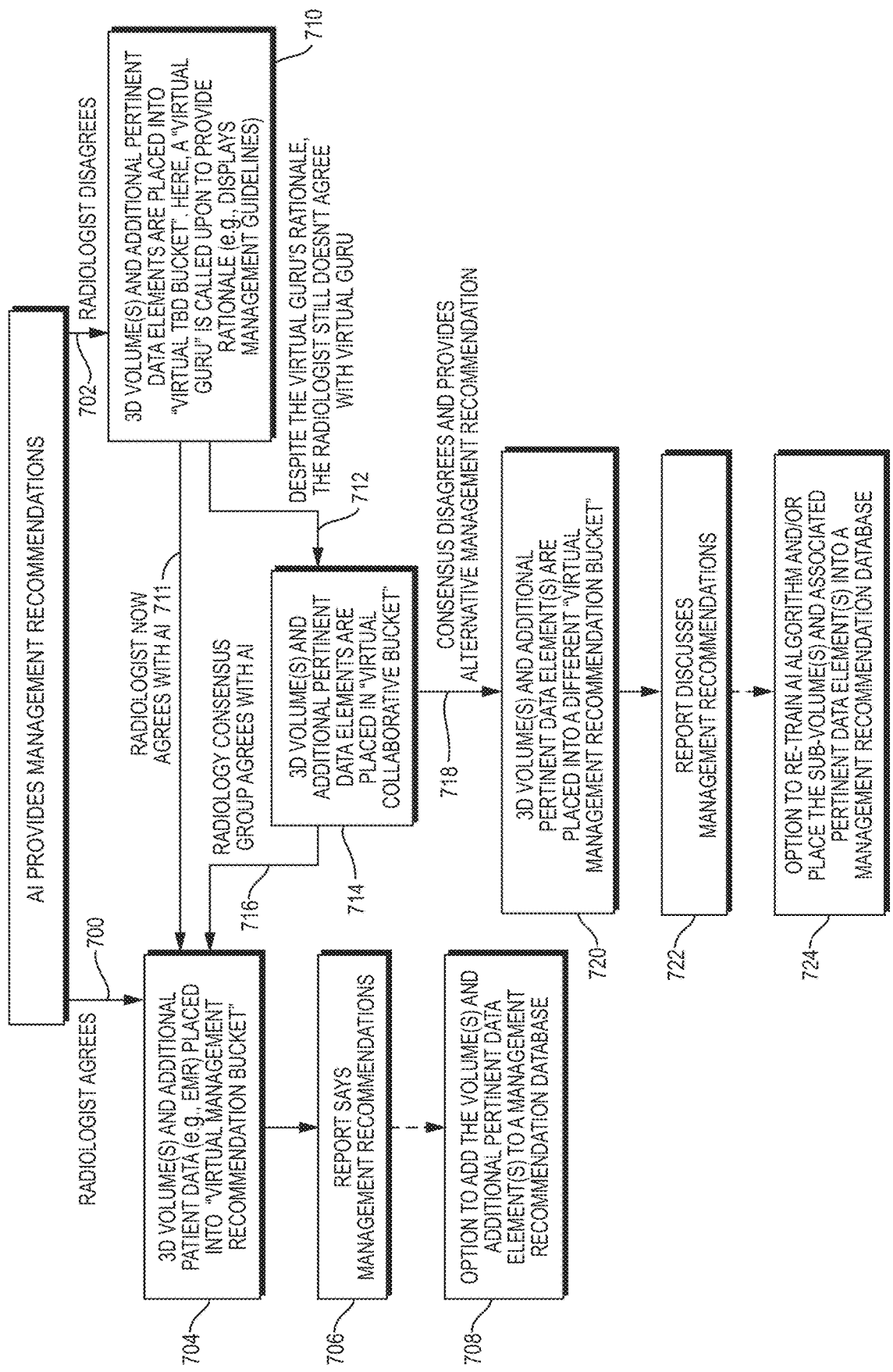
FIG. 7 illustrates a flow diagram for radiologist-assisted machine learning for the scenario wherein the AI reviews the examination and provides further management recommendations.

FIG. 7 illustrates a flow diagram for radiologist-assisted machine learning for the scenario wherein the AI reviews the examination and provides management recommendations. If the radiologist agrees with the AI 700, then the 3D volume(s) and additional pertinent data (e.g., data from the Electronic Medical Record (EMR)) are together placed into the "virtual management recommendation bucket" 704. The radiology report states the management recommendation 706. Then, an option is to add the volume and additional pertinent data element(s) to a management recommendation database 708. If the radiologist disagrees with the AI 602, then the 3D volume(s) and additional pertinent data elements are placed into "virtual TBD bucket" 710. Here, a "virtual guru" is called upon to provide rationale (e.g., displays management guidelines). If the radiologist now agrees with the AI 711, then the 3D volume(s) and additional pertinent data element(s) are added to the "virtual management recommendation bucket" 704. If, despite the virtual guru's rationale, the radiologist still doesn't agree with the virtual guru 612, then the 3D volume(s) and additional pertinent data element(s) are placed into a "virtual collaborative bucket" 714. If the radiology consensus group agrees with the AI 716, then the 3D volume(s) and additional pertinent data element(s) are added to the virtual management recommendation bucket" 704. If the radiology consensus group disagrees and believes an alternative management recommendation is warranted 718, then the 3D volume(s) and additional pertinent data element(s) are placed into a different "virtual management recommendation bucket" 720. Then, the radiology report discusses the management recommendations 722. An option at this juncture is to re-train the AI algorithm and/or place the sub-volume(s) and associated pertinent data element(s) into a management recommendation database 724.

Figure 8:
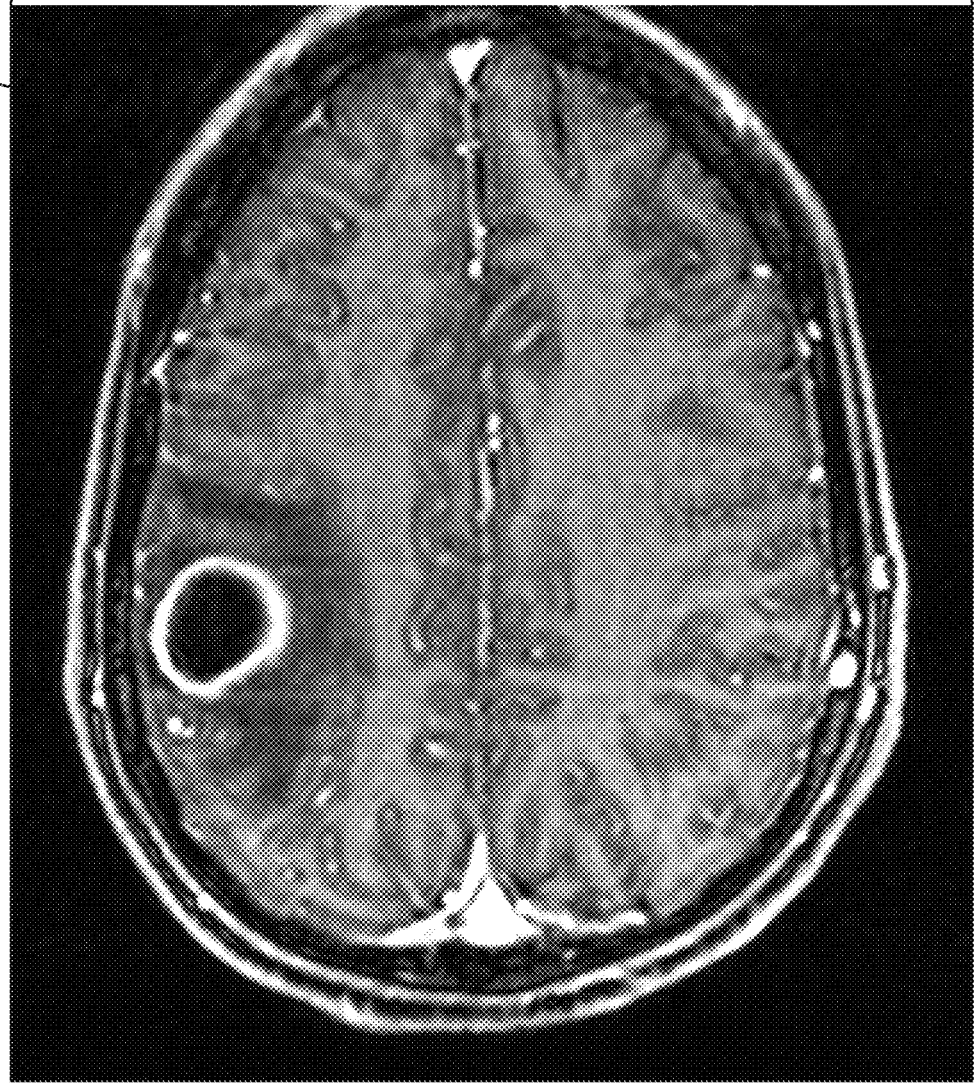
FIG. 8 illustrates the presentation of pertinent data identified via AI search through the electronic medical record that may be relevant to the area of interest that is being examined.

FIG. 8 illustrates the presentation of pertinent data identified via AI search through the electronic medical record that may be relevant to the area of interest that is being examined. The text box is shown in gray 800 and is located above the image 802. In this illustration, the AI has processed the images and has a differential diagnosis including a lung cancer metastasis to the brain. Therefore, it presents multiple potentially relevant data elements to lung cancer in the gray box. Data elements related to other differential diagnoses can also be brought in by the AI algorithm. This process serves to help mitigate some of the potential flaws in the operational system within many medical facilities. First, the physician ordering the medical images may fail to enumerate all the relevant factors impacting the patient's condition. Next, the radiologist must change tasks to obtain different information to obtain the patient's medical records. It is time-consuming to pour through the medical records to extract data that may be relevant. In the presently disclosed system the AI program obtains and processes the records, including but not limited to medical records and patient questionnaires completed upon entry to the medical facility, to obtain information relevant to the patient. Then, this data can be displayed on a conventional 2D monitor or on the headset and manipulated by the radiologist via keyboard or controller.

FIG. 9 provides a flow diagram and illustration for using the 3D cursor in conjunction with radiologist-assisted machine learning. First, as indicated in 900, 2D image slices of medical images 112 to generate a 3D volume 113 per U.S. Pat. No. 8,384,771. The 2D slices are medical images of a type which may include, but is not limited to, MRI, CT, PET, SPECT. The 2D images include pixels with a known inter-pixel spacing and known inter-slice spacing. Centered around each pixel a 3D voxel (e.g., a cube) is created with dimensions in the XY plane equal to the inter-pixel spacing and the Z direction equal to the inter-slice spacing. Next, as indicated in 902, select and encapsulate a sub-volume with a 3D cursor 130. An option at this juncture is to isolate the tissue of interest within the 3D cursor 130, which can be performed via segmentation (i.e., classifying voxels within the volume into discrete tissue types) and then performing filtering (i.e., removing voxels of non-interest and therefore improving visualization of deeper structures when taking an augmented reality, mixed reality or virtual reality 3D imaging approach) per U.S. patent application Ser. No. 15/878, 463. As indicated in 904, computer aided detection (CAD)/ artificial intelligence (AI) is performed on the volume subtended within the 3D cursor 130. As shown, with the exception of the liver, all tissues within the black dashed line 3D cursor 330 have been segmented and filtered (i.e., removed). A small abnormality 910 can be seen within the liver. As indicated in 906, CAD/AI identified abnormality is presented to the radiologist. For example, the conventional cross-sectional images 112 and/or via an additional 3D cursor virtual reality/augmented reality/mixed reality display 106 with reference lines. Note that further segmentation and filtering can be performed, and the isolated abnormality presented in a smaller green dashed line, cube shaped 3D cursor 130. Note that a danger level and certainty level are also provided as detailed in FIG. 12. Finally, as indicated in 908, the radiologist(s) analyze the imaging findings and performs feedback for machine learning.

Figure 10:
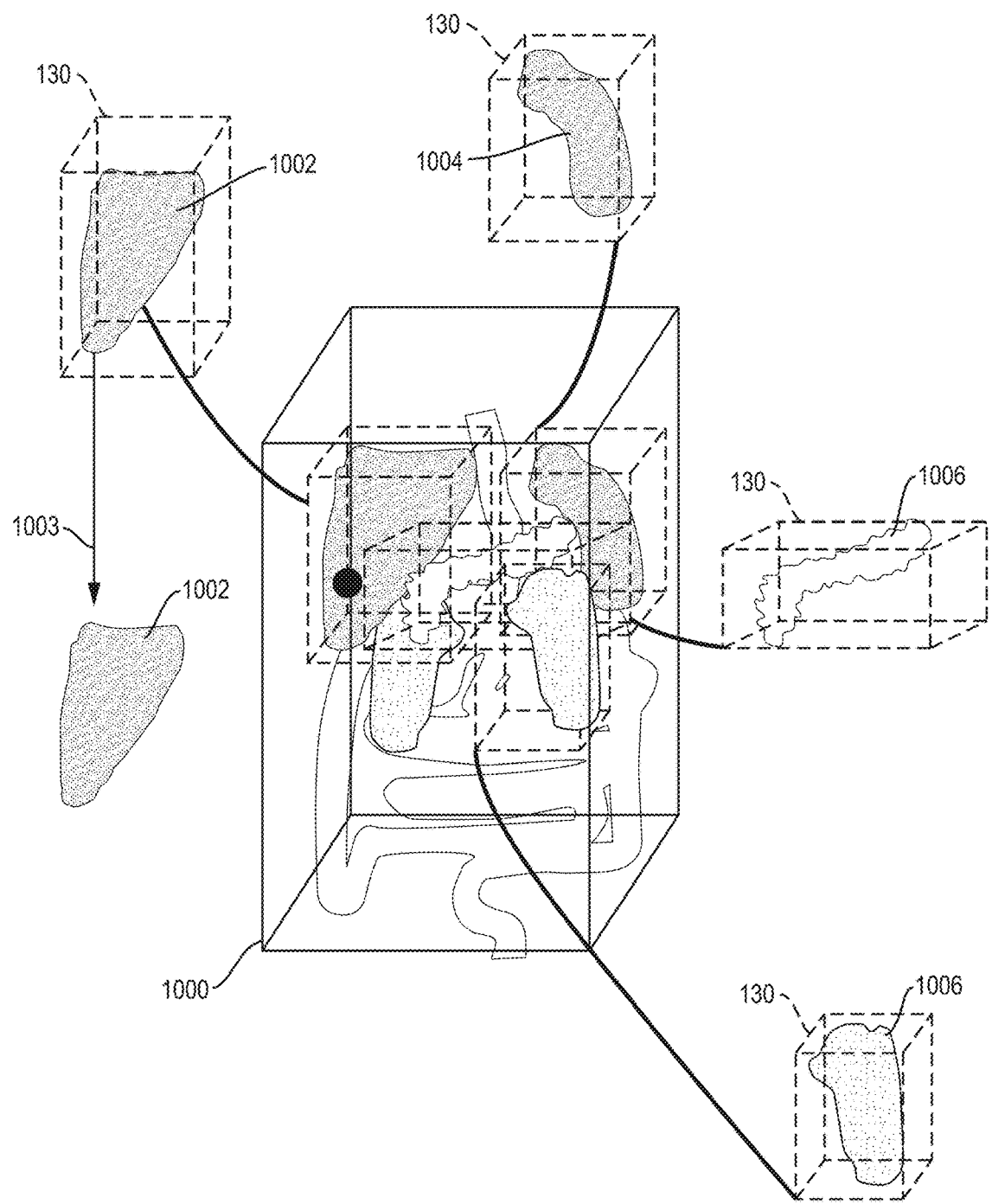
FIG. 10 illustrates the relationship between the composite volume, a sub-volume and volume subtending 3D cursor.

FIG. 10 illustrates the relationship between the composite volume, a sub-volume and volume subtending 3D cursor. In the illustration, multiple shapes of varying shades of gray represent organs of the abdomen and pelvis in the total imaging volume (also referred to as the composite imaging volume) as denoted by 1000. Multiple 3D cursors 130 are shown with each cursor displaying a sub-volume (i.e., a portion of the composite imaging volume). For example, one 3D cursor 130 contains the sub-volume of the liver 1002 with all other tissues within the 3D cursor 130 segmented and filtered (i.e., removed). While the preferred method to visualize and analyze sub-volumes is to keep each sub-volume contained within a 3D cursor, it is also possible to visualize and analyze a sub-volume without being contained in a 3D cursor 130, as shown in 1003. Another example includes a 3D cursor 130 containing the sub-volume of the spleen 1004 with all other tissues within the 3D cursor 130 segmented and filtered (i.e., removed). Another example, includes a 3D cursor 130 containing the sub-volume of the pancreas 1006 with all other tissues within the 3D cursor 130 segmented and filtered (i.e., removed). Finally, another example includes a 3D cursor 130 containing the sub-volume of the left kidney 1006 with all other tissues within the 3D cursor 130 segmented and filtered (i.e., removed). The sub-volumes can each be inspected carefully in the traditional slice-by-slice cross-sectional approach or via advanced 3D viewing such as with an augmented reality headset 106. The diagnostic system provides the radiologist with the capability to review one sub-region by sub-region (i.e., 3D cursors of a size specified by the radiologist for an efficient review) throughout the volume being reviewed in accordance with the check list. Further, the radiologist may decide to move the volume-subtending 3D cursor through the total imaging volume without a discrete organ-by-organ checklist. In this situation, a composite view of cursor path through the 3D volume and re-positioning cursor to initial viewing position can be performed. When the AI/CAD algorithm has identified, the radiologist conducting the review will place special attention to these regions. These regions will be sent to the virtual report bucket (or other bucket) in accordance with the features described throughout this patent. After the review is completed, the radiologist can verify the completeness of the review by invoking display of all of the 3D cursor positions simultaneously. This feature enables the radiologist to see if any portions of the imaging volume that might have been missed during the review and go back, as necessary, to ensure completeness of the review. This process will help ensure a low error rate for the review.

FIG. 11 illustrates the radiologist's workstation without (top) and looking through (bottom) an augmented reality headset where the radiologist can see the virtual bucket only when looking through the AR display. The radiologist would have the ability to virtually pull a selected sub-volume out of the total volume and then place it into a virtual bucket. The preferred approach would be for the radiologist to utilize augmented reality glasses 106 where the radiologist could see virtual buckets on or near his workstation. However, if the radiologist workstation did not have augmented reality glasses, an icon to represent the "virtual bucket" can be used on conventional 2D monitors.

Figure 12:
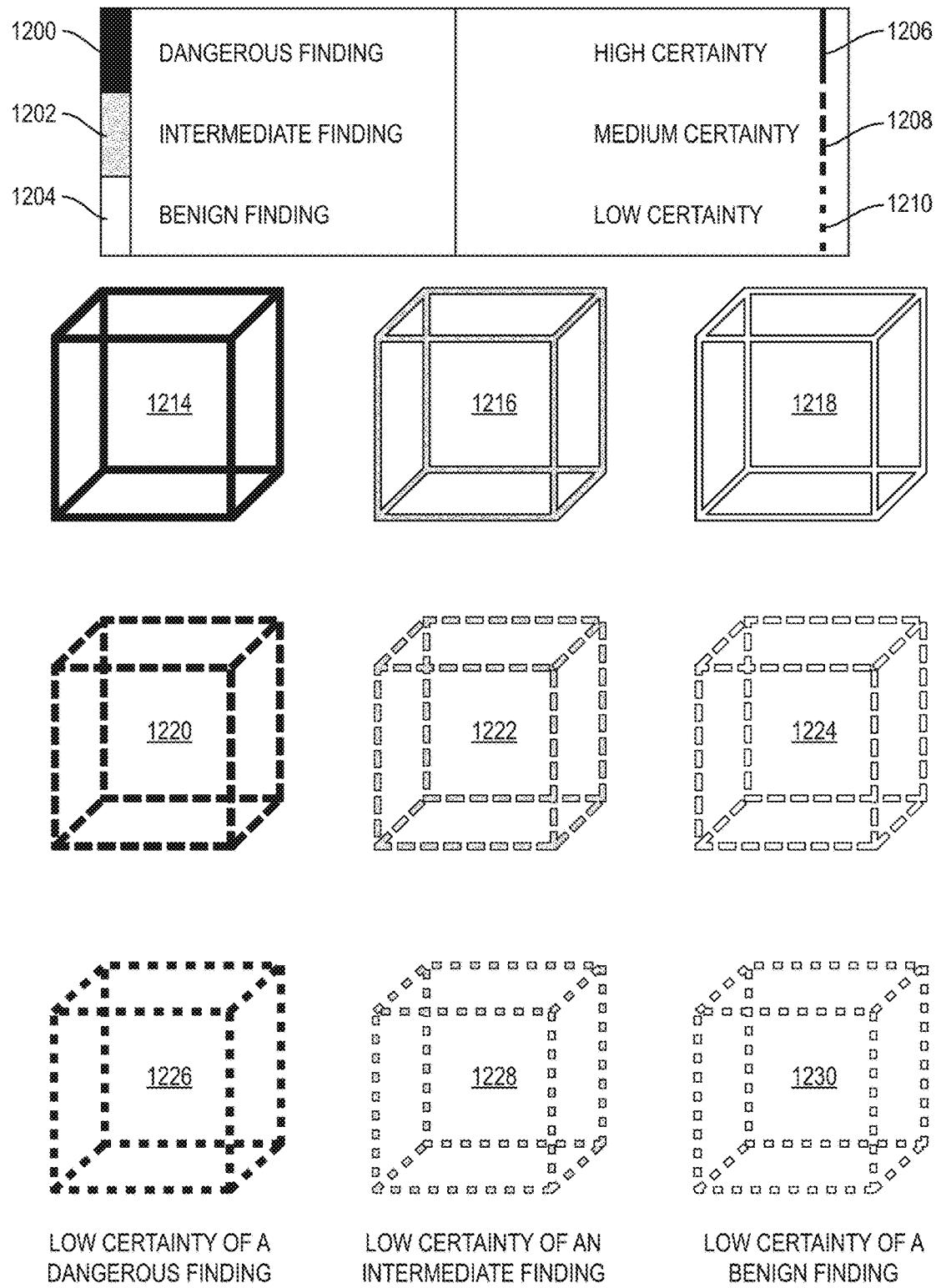
FIG. 12 illustrates an example of how the 3D cursor appearance can change to denote certainty level and severity level of an imaging finding within a sub-volume.

FIG. 12 illustrates an example of how the 3D cursor appearance can change to denote certainty level and severity level of an imaging finding within a sub-volume. The AI and/or CAD performs an initial analysis of the image set. Two key critical pieces information that the radiologist needs to know are the danger of the finding(s) and the certainty level of the finding(s). These two critical pieces can be communicated by changing the appearance of the cursor. The line defining the margins of the 3D cursor can be color-coded to correspond to the danger level of the findings, such as red to denote a dangerous finding (defined as reasonable chance of causing death) 1200, yellow to denote an intermediate finding (defined as likely to cause symptoms, but unlikely to cause death) 1202, and green to denote a benign finding (defined as unlikely to cause symptoms or death) 1204. In addition, the line defining the margins of the 3D cursor can appear solid to correspond to a high level of certainty 1206, dashed to correspond to a medium level of certainty 1208 or dotted to correspond to a low level of certainty 1210. Thus, there are multiple combinations. A red, solid 3D cursor 1214 would indicate high certainty of a dangerous finding. A yellow, solid 3D cursor 1216 would indicate high certainty of an intermediate finding. A green, solid 3D cursor 1218 would indicate a high certainty of a benign finding. A red, dashed 3D cursor 1220 would indicate medium certainty of a dangerous finding. A yellow, dashed 3D cursor 1222 would indicate a medium certainty of an intermediate finding. A green, dashed 3D cursor 1224 would indicate a medium certainty of a benign finding. A red, dotted 3D cursor 1226 would indicate low certainty of a dangerous finding. A yellow, dotted 3D cursor 1228 would indicate low certainty of an intermediate finding. A green, dotted 3D cursor 1230 would indicate low certainty of a benign finding. A preferred option would be for no 3D cursor to be displayed if a checklist item (e.g., organ) has normal findings. When a radiologist opens up a new case, he/she may select "show all red cursors" to see if there are any life-threatening findings and if applicable, notify the ordering physician immediately. During the review process, the radiologist(s) can, on his/her discretion, override the AI/CAD system and change the appearance (color or style of line) such that ordering physicians can see both the AI set of 3D cursors and the radiologist-adjusted set of 3D cursors.

Figure 13:
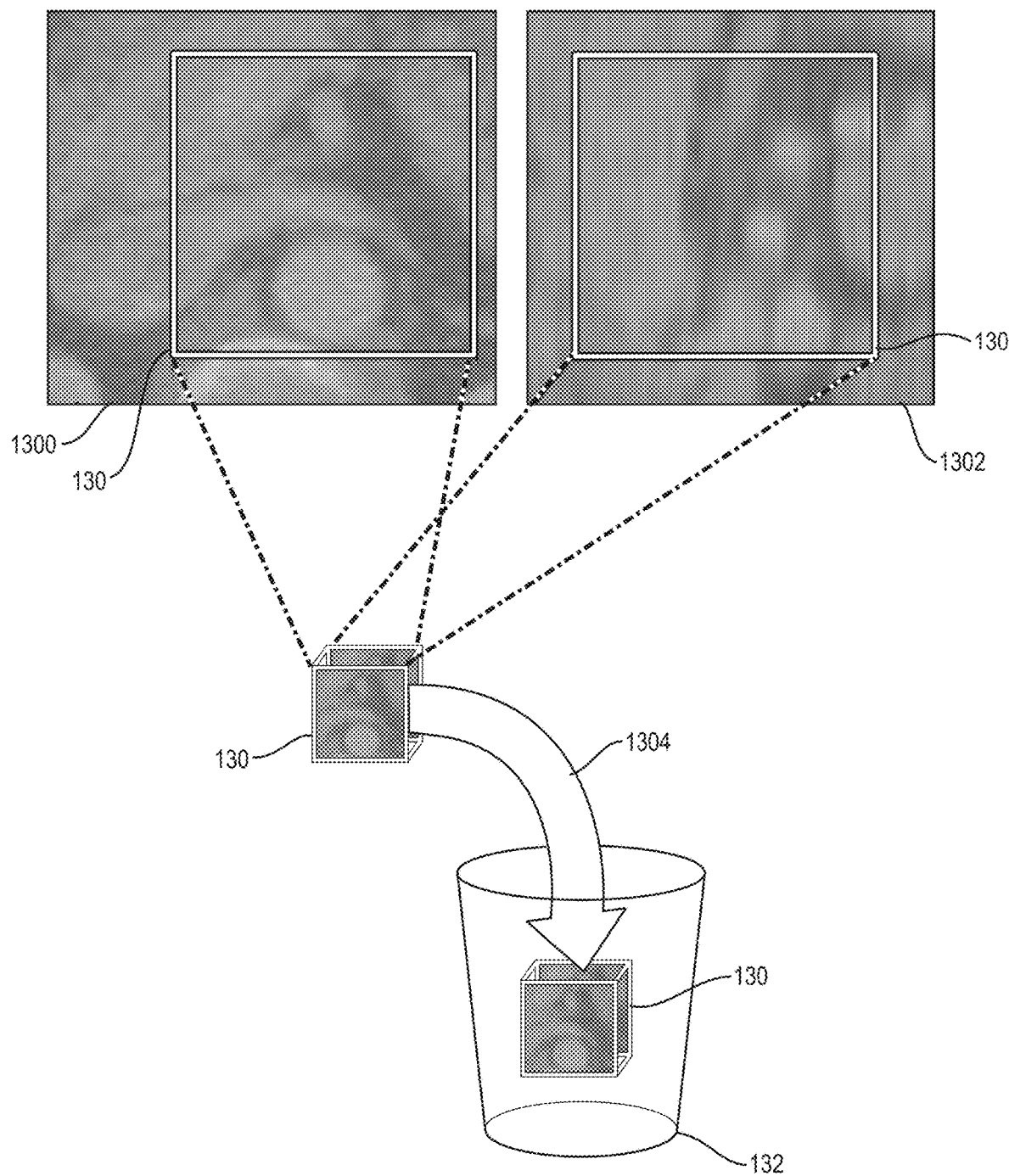
FIG. 13 illustrates placing a normal sub-volume into a "normal anatomy bucket" aspect of radiologist-assisted training.

FIG. 13 illustrates placing a normal sub-volume into a "normal anatomy bucket" aspect of radiologist-assisted training. Axial 1300 and image 1302 contrast enhanced computed tomography (CT) images through the abdomen. Both the axial and coronal images show portions of the superior mesenteric artery (SMA) including the origin and proximal portions. As illustrated, the 3D cursor 130 is used to encapsulate relevant tissue to isolated the sub-volume from the total imaging volume within the CT of the abdomen examination. After encapsulating the origin and proximal portions of the SMA, the radiologist can generate a duplicate copy of the sub-volume within the 3D cursor containing a normal SMA and move 1304 the copied sub-volume within the 3D cursor 130 into a virtual bucket 132, which in this case would be the normal SMA origin contrast-enhanced CT virtual bucket 132. This process of dividing an examination's total imaging volume into sub-volumes and placing sub-volumes into specific bucket can be used for creating radiologist-approved training datasets, which can, in turn, be used to train machine learning algorithms.

Figure 14:
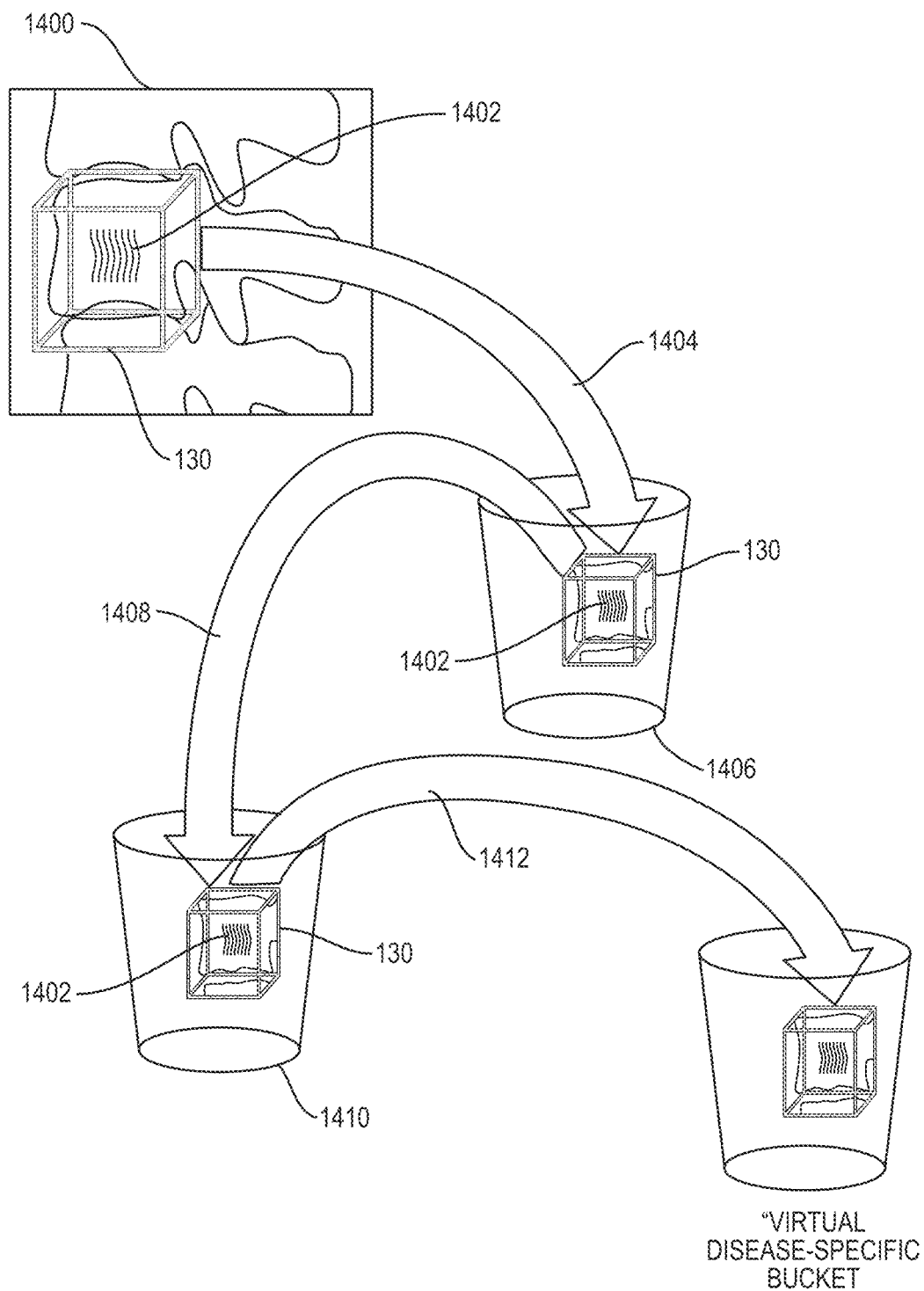
FIG. 14 illustrates the use of the virtual bucket system whereby a volume subtended by a 3D cursor can be moved from one bucket to the next during the analysis phase.

FIG. 14 illustrates the use of the virtual bucket system whereby a volume subtended by a 3D cursor can be moved from one bucket to the next during the analysis phase. During a radiologist review, there may occur multiple clusters of tissue of interest/concern and multiple clusters of tissue that is not of concern. In this scenario, the AI determines that the total imaging volume 1400 is normal, but the radiologist thinks there is an abnormality 1402, but is unsure of what it could be. Therefore, the radiologist places 1404 the 3D cursor 130 containing a sub-volume and the structure of interest 1402 into the "virtual TBD bucket" 1406. The radiologist calls upon the "virtual guru" to find specifically analyze the tissue within the sub-volume encased by the 3D cursor 130. In this scenario, the "virtual guru" concludes that the sub-volume encased by the 3D cursor 130 is normal. The radiologist then places 1408 the 3D cursor 130 and its contents to the "virtual collaborative bucket" 1410. Here a group of radiologists get together, and the consensus is that the structure of interest 1402 within the 3D cursor is a benign vertebral hemangioma. They, the radiologist places 1412 the sub-volume within the 3D cursor into the "benign vertebral hemangioma" virtual bucket 1414. The radiologist may also elect to assign terminology (e.g., "corduroy sign" and "vertebral hemangioma") weighting factors (e.g., "95% certainty") (see FIG. 16 for additional details). Another key benefit of this approach would be the utilization of a "bucket" system for radiologist peer review processes. Peers could review "normal anatomy buckets" for accuracy. Alternatively, they could review "virtual disease specific buckets" for accuracy. Bucket accuracy would be a key factor in determining the skill level of a radiologist.

FIG. 15 illustrates an example radiology report incorporating the 3D cursor and radiologist-assisted machine learning reporting technique. The left hand portion contains each of the checklist items. The column to the right shows the results of each finding on the checklist. For each abnormal finding, an image of the segmented and filtered checklist item is displayed with the 3D cursor with appearance to denote danger and certainty levels is shown at the abnormality. The right-hand portion contains a description of the abnormal findings. If the reviewing the report on a computer, the headset glasses provide a hyper link to volume containing the organ and abnormality encapsulated in the 3D cursor. It is important to note that there must be consistency between the findings within the abdomen. For example, a round sub-centimeter lymph node may be passed by the AI algorithm during the first check. Then, the AI algorithm may, at a later item on the checklist, diagnose a cancerous tumor. Then, the AI algorithm should return through the checklist additional time(s) to re-evaluate all structures in light of the cancerous tumors. For example, a 9 mm round lymph node may on first pass be characterized as benign by the AI algorithm. Then, a cancer is diagnosed. Then, on second pass, the same 9 mm round lymph node may on second pass be characterized as suspicious for metastatic disease.

Figure 16:
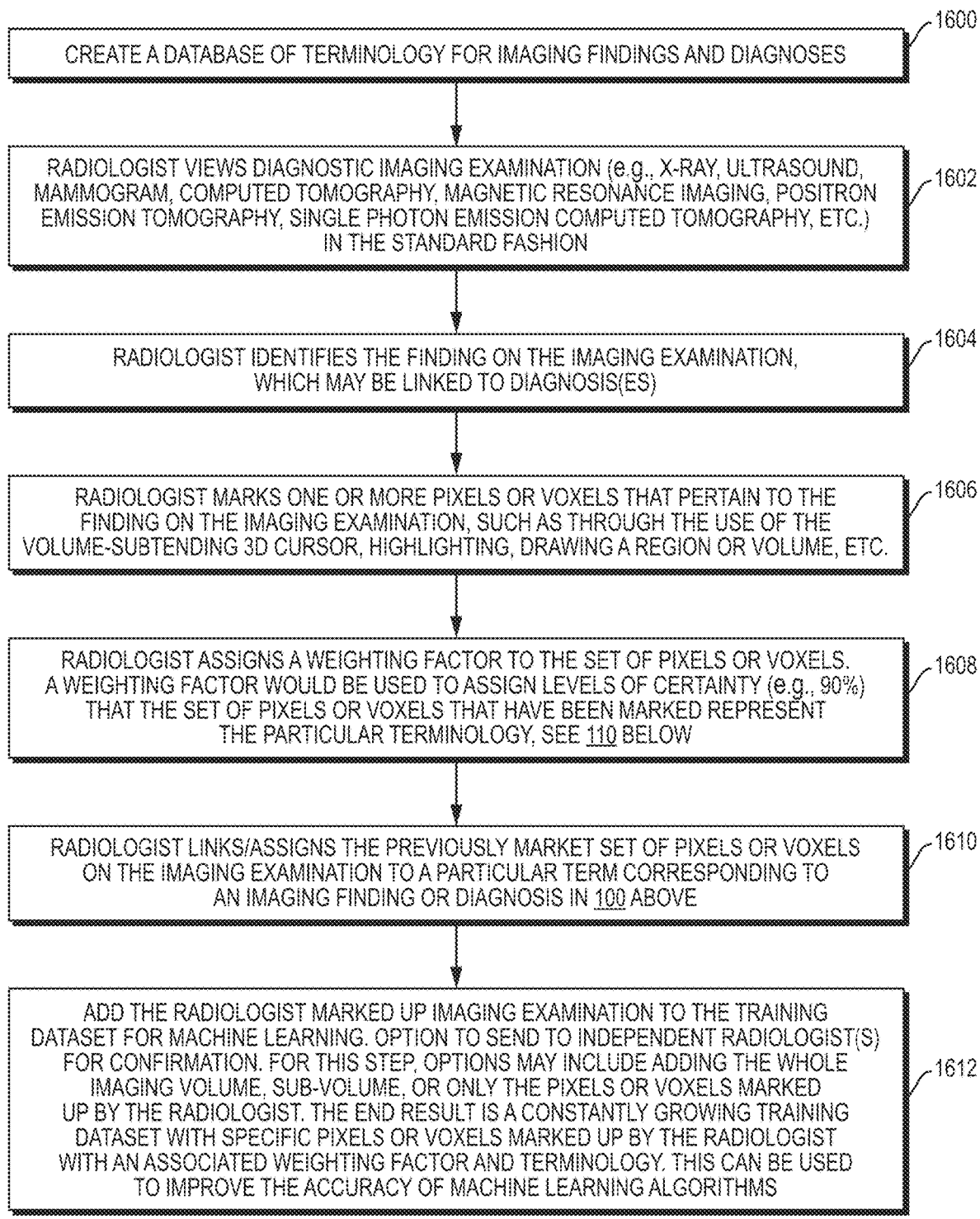
FIG. 16 illustrates a process for creating a radiologist approved machine learning training dataset by incorporating standardized terminology, radiologist image markup and radiologist-assigned weighting factors for radiologist-assisted machine learning.

FIG. 16 illustrates a process for creating a radiologist approved machine learning training dataset by incorporating standardized terminology, radiologist image markup and radiologist-assigned weighting factors for radiologist-assisted machine learning. Machine learning may be based on radiologist review and AI/CAD used to partially automate diagnostic review. In step 1600 a database of terminology is created for image findings and diagnosis. In step 1602 the radiologist views a diagnostic imaging examination in a standard manner using a radiologic imaging and diagnostic system. In step 1604 the radiologist identifies a finding which may be linked to a diagnosis(es) on an imaging examination using the radiologic imaging and diagnostic system. In step 1606 the radiologist marks one or more pixels or voxels of an image that pertain to the finding. This can be through the use of the volume-subtending 3D cursor, highlighting, or drawing a region around the area or volume. In step 1608 the radiologist assigns a weighting factor to the marked set of pixels or voxels. In step 1610 the radiologist links the marked set of pixels or voxels to a term corresponding to a finding or diagnosis as in step 1600 above. In step 1612 the report, pixels and/or voxels marked by the radiologist and associated with a weighting factor, and the terminology are added to a training dataset for machine learning by the imaging and diagnostic system. Options may include adding the whole imaging volume, sub-volume, or only the pixels or voxels marked by the radiologist. The end result is a training dataset with specific pixels or voxels marked up by the radiologist with an associated weighting factor and terminology. This can be used to improve the accuracy of machine learning algorithms.

Figure 17:
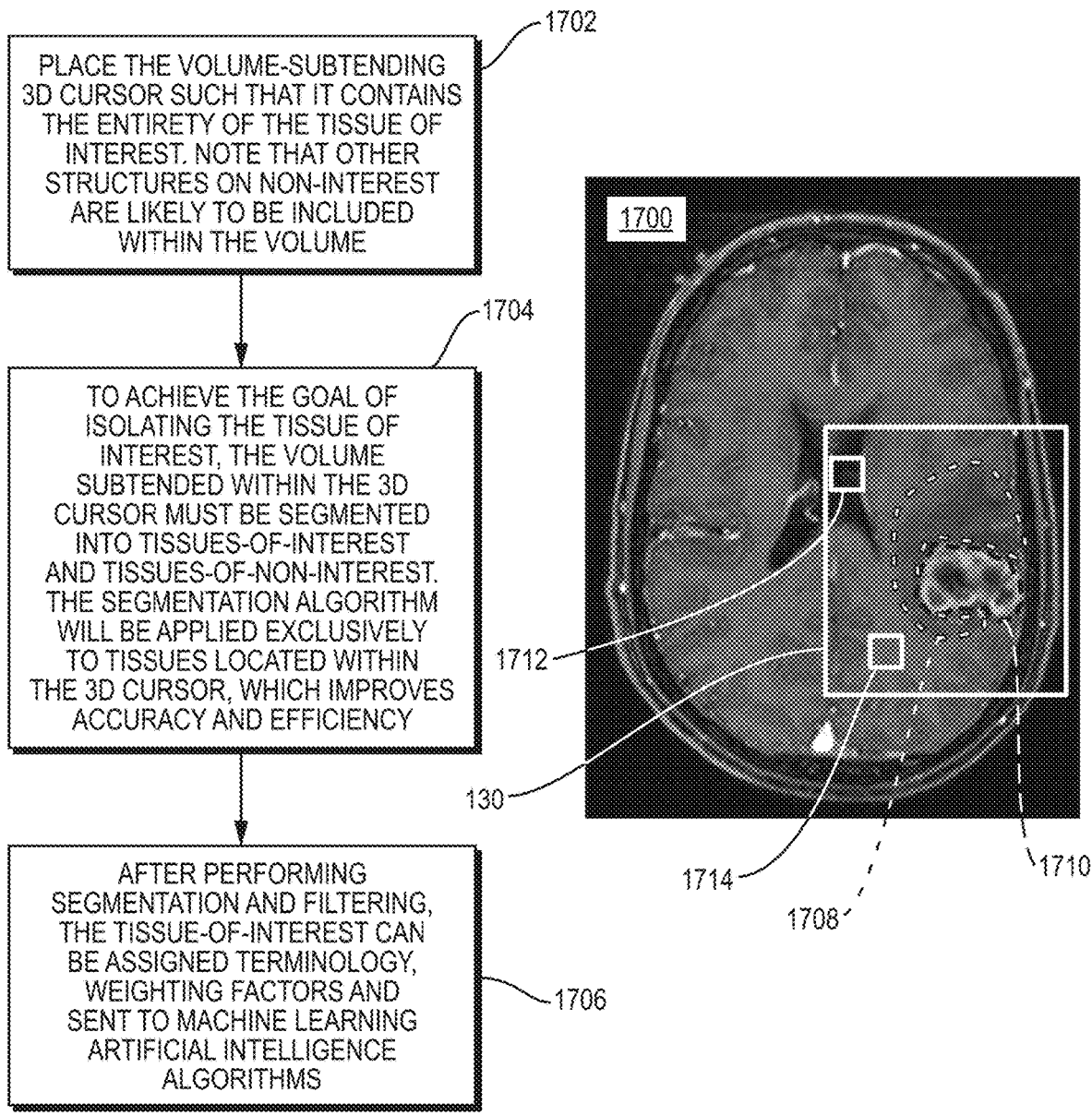
FIG. 17 is a flow diagram and illustration of use of multiple 3D cursor to assist segmentation used in conjunction with radiologist-assisted machine learning via labeling with terminology and weighting factors for radiologist-assisted machine learning.

FIG. 17 is a flow diagram and illustration of use of multiple 3D cursor to assist segmentation used in conjunction with radiologist-assisted machine learning via labeling with terminology and weighting factors for radiologist-assisted machine learning. This can help the AI system can begin to understand that one pathology (e.g., brain tumor) can have multiple components (e.g., non-enhancing component and enhancing component). An efficient segmentation algorithm will help the adoption of RAML into clinical practice. The illustrated example is a 2D MRI slice of a brain 1700 which has a tumor. Segmentation algorithms can be applied to define anatomic structures and/or different components of the tumorous material. Using the controller, the radiologist configures for display the tissue of concern and/or tissue associated with a checklist item. The first step 1700 is to place the 3D cursor 130 over a large volume/area including the entire object of interest, e.g. tumor, and additional tissues of non-interest. To accomplish this, a radiologist can move, size and shape a volume-subtending 3D cursor 130 over a region sufficiently large to encompass the entire brain tumor. In doing this, components of normal brain tissue, cerebrospinal fluid, skull, scalp and air outside of the head will typically be included inside the volume-subtending 3D cursor 130. The second step 1704, the utilization of a 3D cursor 130 can add efficiency and accuracy to this process, by applying a segmentation algorithm only to structures that are within the 3D cursor 130. Then, the margins of the different components of the tumor can be defined (either by the radiologist or by a computer-segmentation algorithm). For example, the segmentation algorithm can divide the tumor into a non-enhancing component 1708 and an enhancing component 1710. To further assist with isolating the tumor, other structures can be labeled and subsequently filtered. For example, a small 3D cursor marks the cerebrospinal fluid 1712. Also, a small 3D cursor marks the normal white matter 1714. The segmented components can be used to train future AI algorithms via the virtual bucket system in the RAML process. After performing segmentation, the tissue of interest can be assigned terminology, weighting factors and used to improve artificial intelligence algorithms 1706. As an example, 3D cursor 1712 containing pixel(s) or voxel(s) of non-interest can be labeled with terminology (e.g., "normal CSF appearance on T1-FSPGR post-contrast sequence", etc.) and weighting factor (e.g., 100% based on neuroradiologist's experience). Also, segmented pixels (or voxels) of interest (i.e., enhancing component of the brain tumor 1708 and non-enhancing component of the brain tumor 1710) can be labeled with terminology (e.g., "enhancing component of glioblastoma multiforme" and "non-enhancing component of glioblastoma multiforme") and weighting factor (e.g., 100% given biopsy and pathology proven).

Figure 18:
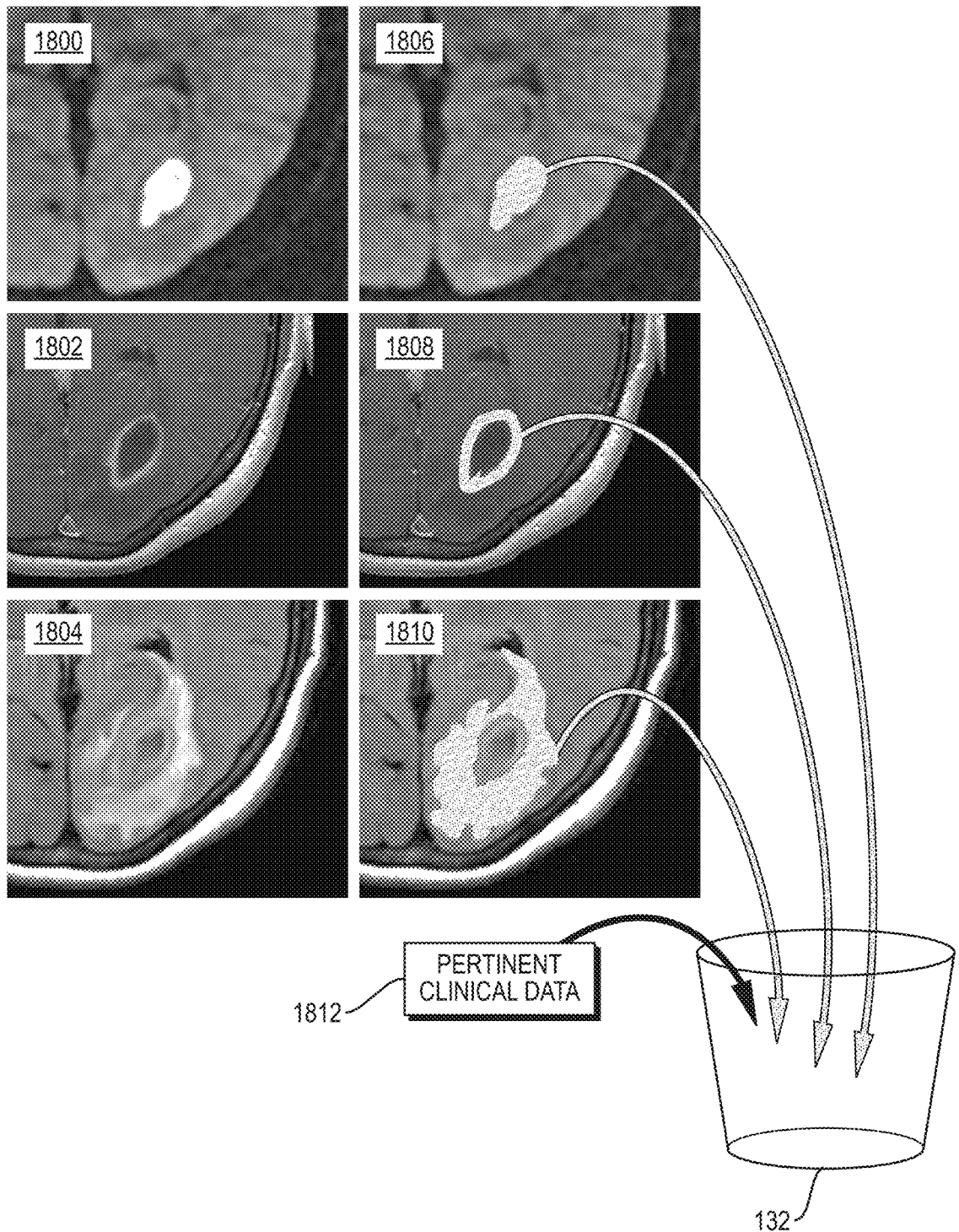
FIG. 18 illustrates image markup and terminology assignment in conjunction with radiologist-assisted machine learning.

FIG. 18 illustrates image markup and terminology assignment in conjunction with radiologist-assisted machine learning. In this figure, three different MM sequences of the brain were obtained. The top left is a diffusion weighted image 1800. The middle left is a post-contrast T1-weighted image 1802. The bottom left is a T2-weighted FLAIR image 1804. The key pixels on the diffusion image have been marked up by a radiologist 1806, assigned imaging finding terminology (i.e., "central restricted diffusion") with an associated certainty level (i.e., there is a 95% certainty that the marked pixels represent true "central restricted diffusion"), assigned a diagnosis terminology (i.e., "brain abscess") with an associated certainty level based on the imaging terminology finding (i.e., in the literature, it is reported that the sensitivity and specificity of the imaging finding of "central restricted diffusion" for the diagnosis of "brain abscess" is 96% and 96%, respectively). Similarly, the key pixels on the post-contrast T1-weighted image are marked up by a radiologist 1808, assigned imaging finding terminology (i.e., "peripheral enhancement) with an associated certainty level (i.e., there is a 99% certainty that the marked pixels on the post-contrast T1-weighted MM represent true "peripheral enhancement"), assigned a diagnosis terminology (i.e., "brain abscess") with an associated certainty level based on imaging terminology findings (i.e., in the literature, a variety of conditions can cause peripheral enhancement including brain metastases, brain abscesses, gliomas, infarction, contusion, demyelinating disease and post-radiation changes; therefore, specificity is low. Experienced radiologists consensus groups can aid in filling in holes where there is no data in the literature on the precise sensitivities and specificities.). Finally, the key pixels on the T2-weighted FLAIR image are marked up by a radiologist 1810, assigned imaging finding terminology (e.g., "surrounding vasogenic edema") with an associated certainty level (i.e., the radiologist is 90% certain that the marked pixels on the T2-weighted FLAIR image represent true "surrounding vasogenic edema"), assigned a diagnostic terminology (i.e., "brain abscess") with an associated certainty level based on imaging terminology findings (i.e., in the literature, a wide variety of conditions can cause vasogenic edema including brain abscesses, contusions, and many others. Therefore, this imaging finding is non-specific. However, since a brain abscess incites an inflammatory response in the brain, it is extremely common to have vasogenic edema and the sensitivity of vasogenic edema for the diagnosis of brain abscess is high.). Finally, pertinent clinical data (e.g. white blood cell count, vital signs, etc.) 1812 will be placed into a virtual bucket 132. After confirmation of the suspected diagnosis of a brain abscess via neurosurgery, the imaging examination, 3D cursor, markup and pertinent clinical data can be added to a database of disease specific pathology, which can be used to refine machine learning and artificial intelligence algorithms.

Figure 19:
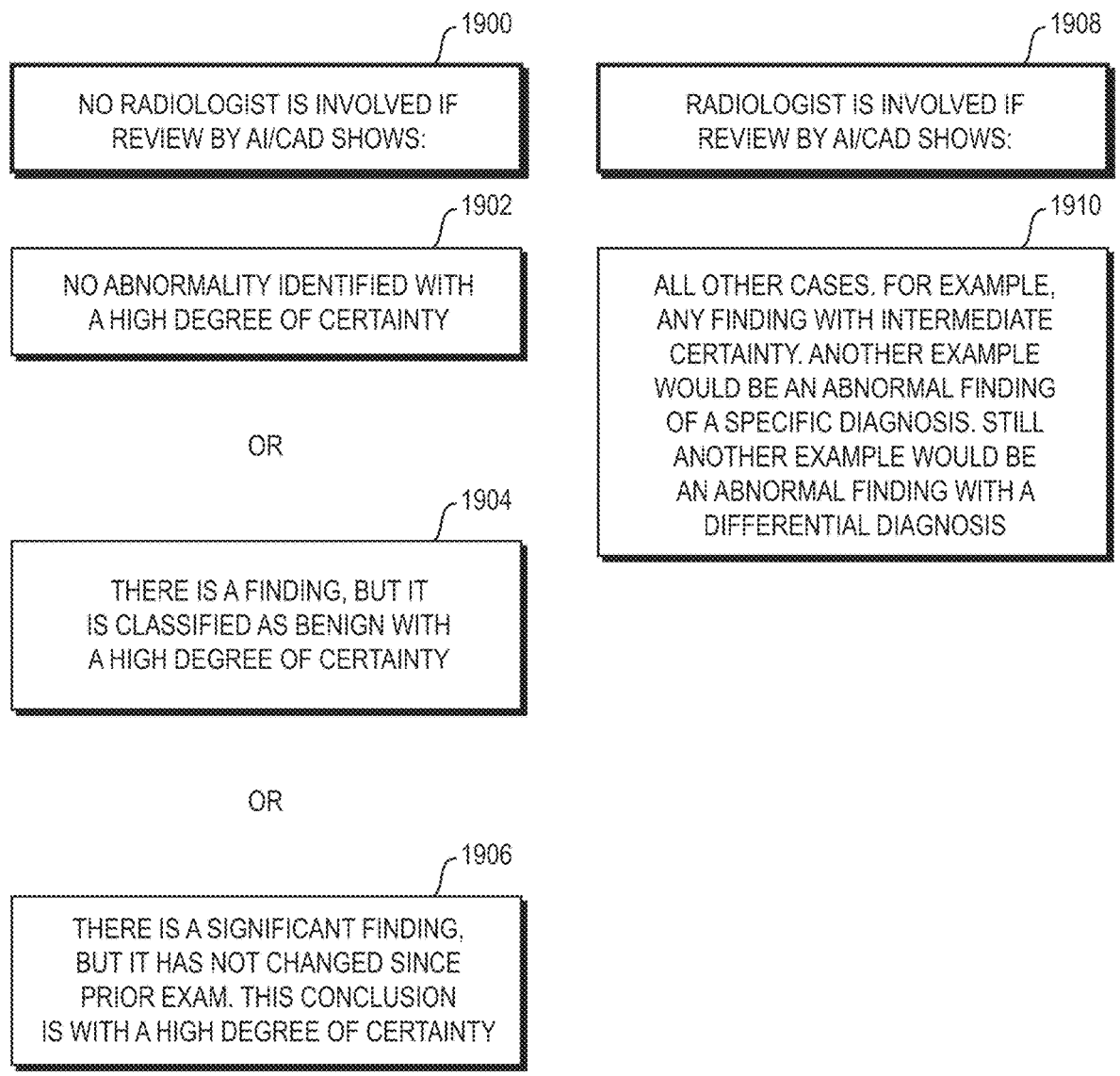
FIG. 19 illustrates a sample set of criteria wherein AI determines whether the imaging examination requires a radiologist's review.

FIG. 19 illustrates a suggested set of criteria wherein AI determines whether the imaging examination requires a radiologist's review. Note that it is conceivable that in the very near term, AI may be extremely accurate in its declaration of a normal finding. In these such situations, a revised process (updated from FIG. 3) may consist of the AI and/or CAD algorithms not requiring a review by a radiologist. However, in the current state (wherein AI is not approaching 100% detection rates), all cases would be passed to a radiologist. The system can be designed such that it does not prompt radiologist review 1900 when AI and/or CAD review concludes that no abnormality is identified 1902, or there is a benign finding classified with a high degree of certainty 1904, or there is a significant finding that has not changed since the prior diagnostic examination 1906. Each factor of the first case can be made contingent on high degree of certainty, information in the patient's reason for visit, and/or information in medical records that would cause suspicion. If the specified conditions hold then the system does not require a review by a radiologist. Radiologist review is prompted 1908 in all other cases 1910. For example, any finding with intermediate certainty would be reviewed by a radiologist. Another example would be an abnormal finding of a specific diagnosis would be reviewed by a radiologist. Still another example would be an abnormal finding with a differential diagnosis would be reviewed by a radiologist. The AI and/or CAD performs an initial diagnosis and uses decision criteria to determine which cases will undergo a radiologist review. Two factors that may be applied are: the danger level and the certainty level of the AI and/or CAD findings. All dangerous cases are provided to a radiologist for further review. Any benign case that is of high certainty is not sent for review by a radiologist. Other combinations would be a policy matter for the medical facility. However, until AI and/or CAD have proven exceptionally reliable for intermediate findings, it would be prudent to pass these cases to a radiologist. Reviewing AI and/or CAD results to date indicates different levels of accuracy for different body parts so, as the checklist is applied, differing levels of certainty will accompany different body parts.

Figure 20:
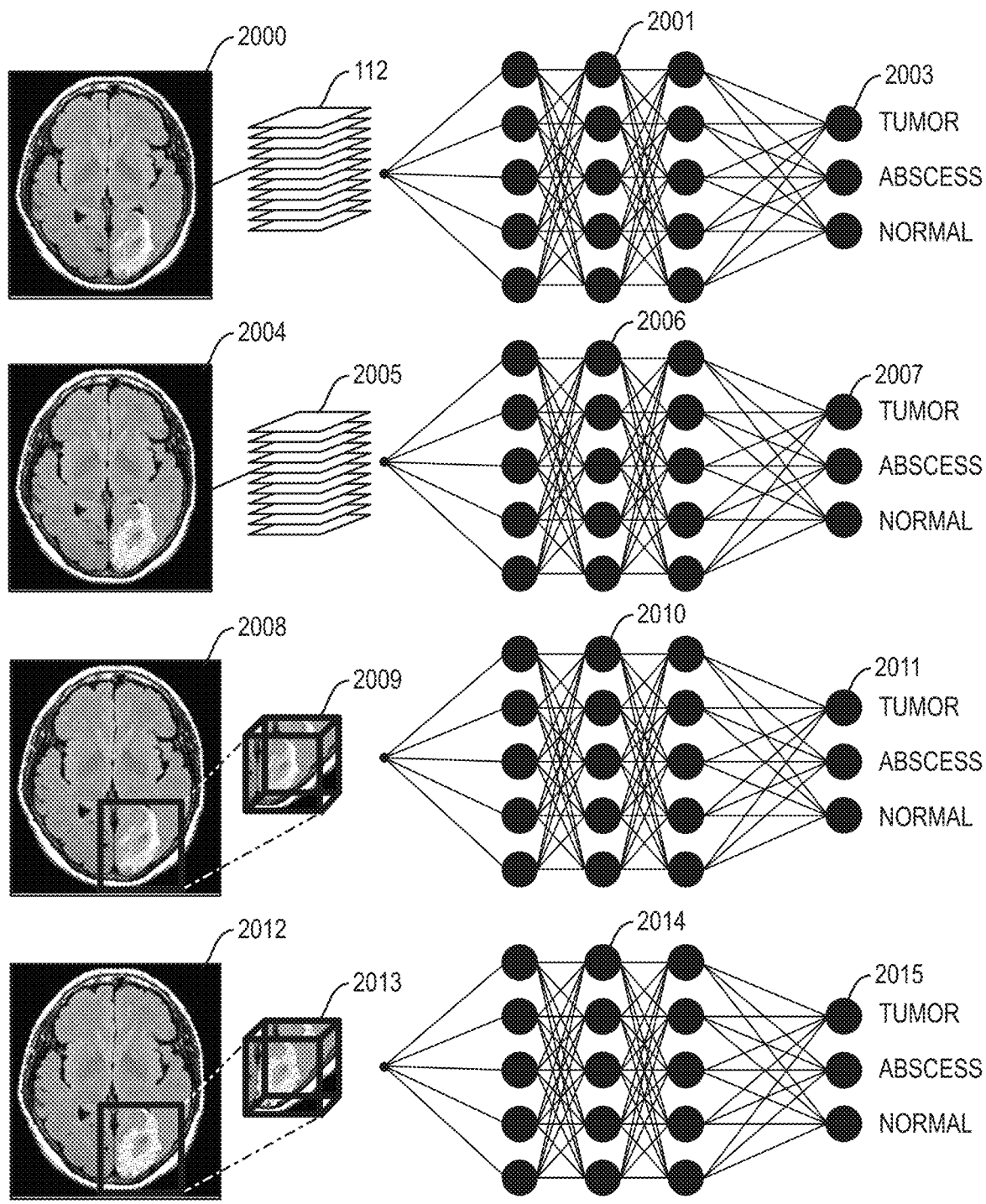
FIG. 20 illustrates the utilization of radiologist image markup and 3D cursors in deep learning algorithms.

FIG. 20 illustrates the utilization of radiologist image markup and 3D cursors in deep learning algorithms. In the first row, a single axial MRI image of the brain 2000 or stack of axial MRI images of the brain 112 can be inputted into a deep learning algorithm consisting of hidden layers 2001 to generate an output 2003 with the top three (or more) differential diagnoses shows with associated rank order or probability. In the second row, a single axial MM image of the brain with some of the pixels marked up by the radiologist with associated terminology and weighting factors 2008 or stack of marked axial MM images of the brain 2009 can be inputted into a deep learning algorithm consisting of hidden layers 2010 to generate an output 2011 with the top three (or more) differential diagnoses shows with associated rank order or probability. In the third row, a single axial MM image of the brain 2008 is illustrated with the 3D cursor marking an imaging finding. A 3D cursor, which encapsulates a sub-volume 2009, can be inputted into a deep learning algorithm consisting of hidden layers 2010 to generate an output 2011 with the top three (or more) differential diagnoses shows with associated rank order or probability. In the fourth row, a single axial MM image of the brain 2012 is illustrated with both the 3D cursor and image markup by the radiologist. A 3D cursor, which encapsulates the sub-volume 2013, can be inputted into a deep learning algorithm consisting of hidden layers 2014 to generate an output 2015 with the top three differential diagnoses shows with associated rank order or probability. A single or combination approach (via averaging) can be implemented at the discretion of a radiologist to determine the final reported rank list in his/her report. For example, two approaches can be chosen (such as the top row algorithm utilizing unmarked image sets and the bottom row algorithm using marked image sets and sub-volumes). The unmarked image set approach may be given a ⅓ weighting factor with the differential diagnosis of Abscess (85% probability) and Tumor (15% probability). The radiologist marked, sub-volume approach may be given a ⅔ weighting factor with the differential diagnosis of Abscess (95% probability) and Tumor (5% probability). Thus, the combined probability reported in the radiologist report would be Abscess 91.7% probability and Tumor 8.3% probability.

What is claimed is:

1. A method comprising:
continuously updating a training dataset while analyzing medical image data with a medical image diagnostic computer having machine-learning capability, comprising the steps of:
using a medical image comprising a CT scan, a MRI scan, a PET scan, an ultrasound or a SPECT scan wherein said medical image comprises a first number of voxels;
using a segmentation algorithm to segment a structure within said medical image wherein said structure comprises a second number of voxels
wherein said second number of voxels is less than said first number of voxels, and
wherein said structure comprises multiple voxels corresponding to a sub-volume of said medical image,
wherein the selected sub-volume corresponds to an item on a diagnostic checklist;
analyzing the selected sub-volume to create a human-generated analysis; and
using the human-generated analysis of the sub-volume to update the training dataset.

2. The method of claim 1 comprising analyzing the selected sub-volume using the training dataset to create a machine-generated analysis with the diagnostic computer before manually analyzing the selected sub-volume.

3. The method of claim 2 comprising resolving disagreement between the human-generated analysis and the machine-generated analysis before using the human-generated analysis to update the training dataset.

4. The method of claim 3 comprising generating a computer-made explanation for the machine-generated analysis.

5. The method of claim 4 comprising updating the human-generated analysis based on the explanation before using the human-generated analysis to update the training dataset.

6. The method of claim 3 comprising prompting a consensus review of the human-generated analysis and machine-generated analysis.

7. The method of claim 6 comprising updating the human-generated analysis based on the consensus review before using the human-generated analysis to update the training dataset.

8. The method of claim 1 comprising the diagnostic computer retrieving and presenting patient-specific data pertinent to the item on the checklist to facilitate creation of the human-generated analysis.

9. The method of claim 1 wherein creating the human-generated analysis comprises creating at least one of: terminology describing findings or diagnosis; marked pixels or voxels; and an indication of certainty of the findings or diagnosis.

10. The method of claim 1 wherein creating the machine-generated analysis comprises creating at least one of: terminology describing findings or diagnosis; marked pixels or voxels; and an indication of certainty of the findings or diagnosis.

11. The method of claim 1 comprising filtering out tissue within the selected sub-volume that is not associated with a finding.

12. The method of claim 1 comprising using a three-dimensional cursor to select said segmented structure.

13. The method of claim 11 comprising automatically re-sizing the three-dimensional cursor to encompass tissue associated with the finding.

14. The method of claim 3 wherein the checklist comprises multiple items, each of which is analyzed, and comprising generating a report based on the human-generated analysis.

15. The method of claim 14 comprising including an indication of disagreement between the human-generated analysis and the machine-generated analysis.

16. The method of claim 1 comprising the three-dimensional cursor visually indicating confidence or dangerousness of a diagnosis.

17. The method of claim 1 comprising placing tissue associated with a finding in a virtual container.

18. The method of claim 17 comprising selecting a virtual container from a normal finding container, a disease-specific container, and differential diagnosis container.

19. An apparatus comprising:
a medical image diagnostic computer having machine-learning capability, the diagnostic computer comprising a non-transitory medium on which is stored computer program logic that continuously updates a training dataset while analyzing medical image data, comprising:
item selection logic that selects a sub-volume of a medical image corresponding to a structure by using a segmentation algorithm to segment said structure,
wherein the selected sub-volume corresponds to an item on a diagnostic checklist,
wherein said medical image comprises a CT scan, a MM scan, a PET scan, an ultrasound or a SPECT scan,
wherein said medical image comprises a first number of voxels,
wherein said structure comprises multiple voxels corresponding to said sub-volume of said medical image,
wherein said structure comprises a second number of voxels, and
wherein said second number of voxels is less than said first number of voxels;
input logic that receives input that creates a human-generated analysis of the selected sub-volume; and update logic that updates the training dataset based on the human-generated analysis.

20. The apparatus of claim 19 comprising diagnostic logic that analyzes the selected sub-volume using the training dataset to create a machine-generated analysis before the human-generated analysis is generated.

* * * * *